United States Patent
Walle-Jensen et al.

(10) Patent No.: US 10,026,159 B2
(45) Date of Patent: Jul. 17, 2018

(54) METHODS AND SYSTEM FOR MANAGEMENT OF DATA DERIVED FROM MEDICAL IMAGING

(71) Applicant: Novadaq Technologies ULC, Burnaby (CA)

(72) Inventors: Jorgen Walle-Jensen, Vancouver (CA); Gregory Vincent Browne, Vancouver (CA)

(73) Assignee: NOVADAQ TECHNOLOGIES ULC, Burnaby (CA)

( * ) Notice: Subject to any disclaimer, the term of this patent is extended or adjusted under 35 U.S.C. 154(b) by 23 days.

(21) Appl. No.: 15/224,342

(22) Filed: Jul. 29, 2016

(65) Prior Publication Data
US 2017/0084012 A1    Mar. 23, 2017

Related U.S. Application Data

(60) Provisional application No. 62/222,631, filed on Sep. 23, 2015.

(51) Int. Cl.
G06K 9/00    (2006.01)
G06T 5/00    (2006.01)
(Continued)

(52) U.S. Cl.
CPC ............ *G06T 5/009* (2013.01); *G06T 7/0012* (2013.01); *G06T 11/206* (2013.01);
(Continued)

(58) Field of Classification Search
CPC ......... G06T 2207/10064; G06T 11/206; G06T 2200/24; G06T 2207/10016; G06T 2210/12; G06T 2210/41; G06T 7/0012
See application file for complete search history.

(56) References Cited

U.S. PATENT DOCUMENTS

| 8,488,863 B2 | 6/2013 | Boucheron |
| 9,892,513 B2 | 2/2018 | Gurevich et al. |

(Continued)

FOREIGN PATENT DOCUMENTS

| WO | WO-1999/028856 A1 | 6/1999 |
| WO | WO-2014/139021 A1 | 9/2014 |

(Continued)

OTHER PUBLICATIONS

Lauer, G. et al. (Jul. 2000). "Expression and Proteolysis of Vascular Endothelial Growth Factor is Increased in Chronic Wounds," *Journal of Investigative Dermatology* 115(1):12-18.

(Continued)

*Primary Examiner* — Li Liu
(74) *Attorney, Agent, or Firm* — Morrison & Foerster LLP

(57) ABSTRACT

Systems and methods for storing data for a first time series of fluorescence images of the subject acquired during a first imaging session, storing data for a second time series of fluorescence images of the subject acquired during a second imaging session, receiving a request to view attributes of the subject, and in response to receiving the request, displaying a user interface on the display, the user interface comprising a first image showing a visually enhanced attribute of the subject, wherein the first image is generated from the data for the first time series of fluorescence images, and a second image showing the visually enhanced attribute of the subject, wherein the second image is generated from the data for the second time series of fluorescence images.

41 Claims, 15 Drawing Sheets
(9 of 15 Drawing Sheet(s) Filed in Color)

(51) Int. Cl.
*G06T 7/00* (2017.01)
*G06T 11/20* (2006.01)

(52) U.S. Cl.
CPC .................. *G06T 2200/24* (2013.01); *G06T 2207/10064* (2013.01); *G06T 2207/20208* (2013.01); *G06T 2210/12* (2013.01)

(56) References Cited

U.S. PATENT DOCUMENTS

| | | | | |
|---|---|---|---|---|
| 2001/0036304 | A1* | 11/2001 | Yang | G06K 9/00127 382/132 |
| 2002/0183621 | A1 | 12/2002 | Pfeiffer et al. | |
| 2007/0016029 | A1* | 1/2007 | Donaldson | A61B 5/7475 600/437 |
| 2008/0101678 | A1 | 5/2008 | Suliga et al. | |
| 2008/0125643 | A1* | 5/2008 | Huisman | A61B 5/055 600/420 |
| 2009/0097723 | A1* | 4/2009 | Washburn | A61B 8/06 382/128 |
| 2009/0290017 | A1 | 11/2009 | Shibasaki | |
| 2010/0215226 | A1* | 8/2010 | Kaufman | G06K 9/342 382/128 |
| 2011/0071403 | A1 | 3/2011 | Sevick-Muraca et al. | |
| 2011/0311026 | A1* | 12/2011 | Lalena | A61B 6/4405 378/98.5 |
| 2012/0070044 | A1* | 3/2012 | Avinash | G06K 9/3233 382/128 |
| 2012/0214180 | A1 | 8/2012 | Hess et al. | |
| 2013/0051651 | A1* | 2/2013 | Leary | G06T 7/0012 382/133 |
| 2013/0195329 | A1 | 8/2013 | Canda et al. | |
| 2013/0345560 | A1 | 12/2013 | Ferguson, Jr. et al. | |
| 2014/0049555 | A1* | 2/2014 | Bzdusek | G06T 7/0014 345/589 |
| 2015/0004630 | A1 | 1/2015 | Lange et al. | |
| 2016/0253800 | A1 | 9/2016 | Gurevich et al. | |
| 2016/0314585 | A1* | 10/2016 | Thomas | G06T 7/0012 |

FOREIGN PATENT DOCUMENTS

| | | |
|---|---|---|
| WO | WO-2015/052710 A1 | 4/2015 |
| WO | WO-2016/087589 A1 | 6/2016 |
| WO | WO-2016/123705 A1 | 8/2016 |

OTHER PUBLICATIONS

Leung, D.W. et al. (Dec. 8, 1989). "Vascular Endothelial Growth Factor is a Secreted Angiogenic Mitogen," *Science* 246:1306-1309.
Wietecha, M.S. et al. (2013) "Mechanisms of Vessel Regression: Toward an Understanding of the Resolution of Angiogenesis," *Current Topics in Microbiology and Immunology* 367:3-32.
International Search Report and Written Opinion dated May 5, 2016 for PCT/CA2016/050092 filed Feb. 2, 2016, seven pages.
Unpublished U.S. Appl. No. 15/224,088, filed Jul. 29, 2016 entitled, "Methods and Systems for Assessing Healing of Tissue,".
Gannot et al. (Nov. 11, 2004). "Fluorescence Imaging of Lesions, Deep Beneath Tissue Surface." 17th Annual Meeting of the IEEE Lasers and Electro-Optics Society, pp. 898-899.
International Preliminary Report on Patentability dated Aug. 17, 2017, for PCT/CA2016/050092 filed Feb. 2, 2016, five pages.
International Preliminary Report on Patentability dated Oct. 24, 2017, for PCT/IB2016/00124 filed on Feb. 5, 2016, seven pages, (with English Translation).
International Search Report and Written Opinion dated Apr. 22, 2016 for PCT/IB2016/00124 filed on Feb. 5, 2016, ten pages, (with English Translation).
International Search report and Written Opinion dated Nov. 14, 2017, for PCT Application No. PCT/CA2017/050912 filed on Jul. 28, 2017, thirteen pages.
Invitation to Pay Additional Fees and, where Applicable, Protest Fee dated Oct. 5, 2017, for PCT Application No. PCT/CA2017/050912 filed on Jul. 28, 2017, two pages.
U.S. Non-Final Office Action dated Aug. 24, 2017, for U.S. Appl. No. 15/013,945, filed Feb. 2, 2016, eight pages.
U.S. Notice of Allowance dated Sep. 28, 2017, for U.S. Appl. No. 15/013,945, filed Feb. 2, 2016, eight pages.
Unpublished U.S. Appl. No. 15/663,290, filed Jul. 28, 2017 entitled, "Methods and Systems for Characterizing Tissue of a Subject Utilizing a Machine Learning."
International Preliminary Report on Patentability dated Apr. 5, 2018, for PCT/IB2016/001214 filed Jul. 29, 2016, seven pages.

\* cited by examiner

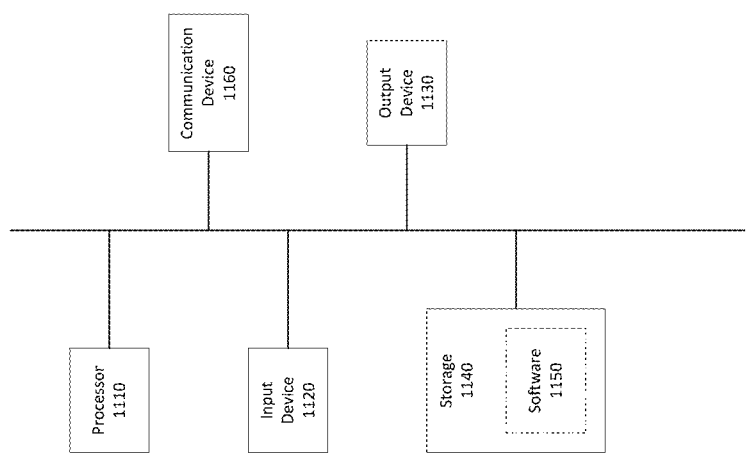

METHODS AND SYSTEM FOR MANAGEMENT OF DATA DERIVED FROM MEDICAL IMAGING

CROSS-REFERENCE TO RELATED APPLICATIONS

This application claims priority to U.S. Provisional Application Ser. No. 62/222,631 filed on Sep. 23, 2015, entitled "METHODS AND SYSTEMS FOR MANAGEMENT OF DATA DERIVED FROM MEDICAL IMAGING," which is hereby incorporated by reference in its entirety.

TECHNICAL FIELD

The present invention relates generally to the field of medical imaging, and more particularly to management of data derived from medical imaging.

BACKGROUND

Currently available technologies for management of clinical data such as, for example, clinical data derived from fluorescence imaging are cumbersome for clinicians to use, with unfriendly and complex workflows often including a number of tool options that are better suited for research rather than clinical use. Such tools can also have slow performance characteristics such as long load times of the medical data and slow application response to user actions, which contribute to users resisting using such tools in the clinical setting.

BRIEF SUMMARY OF THE INVENTION

Systems and methods in accordance with the various embodiments provide an intuitive and user friendly user interface with modality-specific workflows which facilitate access to advanced analysis tools for inexperienced and experienced users, which may be used in the analysis of any clinically relevant information such as blood flow, tissue perfusion, or a combination thereof. The systems and methods can provide a user interface for displaying data derived from medical imaging of a subject over a series of encounters. The user interface can include images showing visually enhanced attributes of tissue and/or anatomy of the imaged subject. The changes in the attributes from one imaging session to another, which can be easily seen by comparing one image to another, can be used to easily assess treatment progress of the imaged tissue and/or anatomy of the subject.

According to some embodiments, a system for displaying an attribute of a subject comprises a display, one or more processors, memory, one or more programs stored in the memory and configured to be executed by the one or more processors, the one or more programs including instructions for: storing data for a first time series of fluorescence images of the subject acquired during a first imaging session, storing data for a second time series of fluorescence images of the subject acquired during a second imaging session, receiving a request to view attributes of the subject, and in response to receiving the request, displaying a user interface on the display, the user interface comprising a first image showing a visually enhanced attribute of the subject, wherein the first image is generated from the data for the first time series of fluorescence images, and a second image showing the visually enhanced attribute of the subject, wherein the second image is generated from the data for the second time series of fluorescence images.

In any of these embodiments, the first and second images may comprise a maximum perfusion image or map, a maximum fluorescence intensity image or map, a coefficient-derived image or map, a fluorescence intensity variability image or map, an egress rate image or map, an ingress onset image or map, or a combination thereof.

In any of these embodiments, the first and second images may comprise color contrast. In any of these embodiments, the first and second images may comprise grayscale contrast. In any of these embodiments, the attribute may be an attribute of tissue of the subject.

In any of these embodiments, the one or more programs may include instructions for receiving a selection of the first image and, in response to receiving the selection, enlarging the first image. In any of these embodiments, the one or more programs may include instructions for receiving a selection of the second image and replacing the enlarged first image with an enlarged second image.

In any of these embodiments, at least some of the data for the first time series and at least some of the data for the second time series may comprise raw data, pre-processed data or a combination thereof.

In any of these embodiments, the pre-processed data may be generated by one or more of cropping, spatially aligning, and determination of baseline intensity. In any of these embodiments, the user interface may comprise a graph of a characteristic of a region of interest within at least one of the first image and the second image.

In any of these embodiments, the graph may comprise a change in intensity over time that is indicative of a healing state of tissue of the subject. In any of these embodiments, the graph may comprise a first curve associated with the first image and a second curve associated with the second image.

In any of these embodiments, the user interface may include a quantification of a healing state of tissue of the subject associated with each imaging session. In any of these embodiments, a pixel value of the first image may be calculated from corresponding pixel values of the first time series of fluorescence images.

In any of these embodiments, the one or more programs may include instructions for, in response to receiving the request, calculating a baseline from the data for the first time series of fluorescence images and the data for the second time series of fluorescence images, wherein the first and second images are generated based on the baseline.

In any of these embodiments, the baseline may be calculated from a minimum intensity value or an average intensity value for both of the data for the first time series of fluorescence images and the data for the second time series of fluorescence images.

In any of these embodiments, the first image may be scaled to a range of values and the second image may be scaled to the range of values. In any of these embodiments, the system may be a handheld electronic device.

According to some embodiments, a method for displaying an attribute of a subject comprises, at a computer system comprising one or more processors, memory, and a display, storing data for a first time series of fluorescence images of the subject acquired during a first imaging session, storing data for a second time series of fluorescence images of the subject acquired during a second imaging session, receiving a request to view attributes of the subject, and in response to receiving the request, displaying a user interface on the display, the user interface comprising a first image showing a visually enhanced attribute of the subject, wherein the first image is generated from the data for the first time series of fluorescence images, and a second image showing the visually enhanced attribute of the subject, wherein the second image is generated from the data for the second time series of fluorescence images.

In any of these embodiments, the first and second images may comprise a maximum perfusion image or map, a maximum fluorescence intensity image or map, a coefficient-derived image or map, a fluorescence intensity variability image or map, an egress rate image or map, an ingress onset image or map, or a combination thereof.

In any of these embodiments, the first and second images may comprise color contrast. In any of these embodiments, the first and second images may comprise grayscale contrast. In any of these embodiments, the attribute may be an attribute of tissue of the subject.

In any of these embodiments, the method may include receiving a selection of the first image and, in response to receiving the selection, enlarging the first image. In any of these embodiments, the method may include receiving a selection of the second image and replacing the enlarged first image with an enlarged second image.

In any of these embodiments, at least some of the data for the first time series and at least some of the data for the second time series may comprise raw data, pre-processed data or a combination thereof.

In any of these embodiments, the pre-processed data may be generated by one or more of cropping, spatially aligning, and determination of baseline intensity. In any of these embodiments, the user interface may comprise a graph of a characteristic of a region of interest within at least one of the first image and the second image.

In any of these embodiments, the graph may comprise a change in intensity over time that is indicative of a healing state of tissue of the subject. In any of these embodiments, the graph may comprise a first curve associated with the first image and a second curve associated with the second image.

In any of these embodiments, the user interface may include a quantification of a healing state of tissue of the subject associated with each imaging session. In any of these embodiments, a pixel value of the first image may be calculated from corresponding pixel values of the first time series of fluorescence images.

In any of these embodiments, the method may include, in response to receiving the request, calculating a baseline from the data for the first time series of fluorescence images and the data for the second time series of fluorescence images, wherein the first and second images are generated based on the baseline.

In any of these embodiments, the baseline may be calculated from a minimum intensity value or an average intensity value for both of the data for the first time series of fluorescence images and the data for the second time series of fluorescence images.

In any of these embodiments, the first image may be scaled to a range of values and the second image may be scaled to the range of values. In any of these embodiments, the system may be a handheld electronic device.

A non-transitory computer readable storage medium storing one or more programs, the one or more programs comprising instructions, which when executed by an electronic system with a display, cause the system to perform a method comprising storing data for a first time series of fluorescence images of the subject acquired during a first imaging session, storing data for a second time series of fluorescence images of the subject acquired during a second imaging session, receiving a request to view attributes of the subject, and in response to receiving the request, displaying a user interface on the display, the user interface comprising a first image showing a visually enhanced attribute of the subject, wherein the first image is generated from the data for the first time series of fluorescence images, and a second image showing the visually enhanced attribute of the subject, wherein the second image is generated from the data for the second time series of fluorescence images.

In any of these embodiments, the first and second images may comprise a maximum perfusion image or map, a maximum fluorescence intensity image or map, a coefficient-derived image or map, a fluorescence intensity variability image or map, an egress rate image or map, an ingress onset image or map, or a combination thereof.

In any of these embodiments, the first and second images may comprise color contrast. In any of these embodiments, the first and second images may comprise grayscale contrast. In any of these embodiments, the attribute may be an attribute of tissue of the subject.

In any of these embodiments, the one or more programs may include instructions for receiving a selection of the first image and, in response to receiving the selection, enlarging the first image. In any of these embodiments, the one or more programs may include instructions for receiving a selection of the second image and replacing the enlarged first image with an enlarged second image.

In any of these embodiments, at least some of the data for the first time series and at least some of the data for the second time series may comprise raw data, pre-processed data or a combination thereof. In any of these embodiments, the pre-processed data may be generated by one or more of cropping, spatially aligning, and determination of baseline intensity.

In any of these embodiments, the user interface may comprise a graph of a characteristic of a region of interest within at least one of the first image and the second image. In any of these embodiments, the graph may comprise a change in intensity over time that is indicative of a healing state of tissue of the subject.

In any of these embodiments, the graph may comprise a first curve associated with the first image and a second curve associated with the second image. In any of these embodiments, the user interface may include a quantification of a healing state of tissue of the subject associated with each imaging session.

In any of these embodiments, a pixel value of the first image may be calculated from corresponding pixel values of the first time series of fluorescence images. In any of these embodiments, the one or more programs may include instructions for, in response to receiving the request, calculating a baseline from the data for the first time series of fluorescence images and the data for the second time series of fluorescence images, wherein the first and second images are generated based on the baseline.

In any of these embodiments, the baseline may be calculated from a minimum intensity value or an average intensity value for both of the data for the first time series of fluorescence images and the data for the second time series of fluorescence images.

In any of these embodiments, the first image may be scaled to a range of values and the second image may be scaled to the range of values. In any of these embodiments, the system may be a handheld electronic device.

According to some embodiments, a system for displaying an attribute of a subject comprises a display, one or more processors, memory, one or more programs stored in the memory and configured to be executed by the one or more processors, the one or more programs including instructions for displaying a user interface on the display, the user interface comprising a first image showing a visually enhanced attribute of the subject, wherein the first image is based on data from a first fluorescence imaging session, and a second image showing the visually enhanced attribute of the subject, wherein the second image is based on data from a second fluorescence imaging session, and determining a region of interest within the first image and the second image, generating metrics of the attribute of the subject within the region of interest for each of the first and second images, and updating the user interface to display the metrics.

In any of these embodiments, the region of interest within the first image may be determined based on an input by the user. In any of these embodiments, the input by the user may comprise insertion of a first bounding box on a portion of the user interface associated with the region of interest for the first image.

In any of these embodiments, the user interface may comprise a third image that is based on data from the first fluorescence imaging session, and the one or more programs may include instructions for automatically inserting a second bounding box on a portion of the user interface associated with the region of interest of the second image.

In any of these embodiments, the first and second images may comprise a maximum perfusion image or map, a maximum fluorescence intensity image or map, a coefficient-derived image or map, a fluorescence intensity variability image or map, an egress rate image or map, an ingress onset image or map, or a combination thereof.

In any of these embodiments, the first and second images may comprise color contrast. In any of these embodiments, the first and second images may comprise grayscale contrast. In any of these embodiments, the attribute may be an attribute of tissue of the subject.

According to some embodiments, a method for displaying an attribute of a subject, the method comprises, at a computer system comprising one or more processors, memory, and a display, displaying a user interface on the display, the user interface comprising a first image showing a visually enhanced attribute of the subject, wherein the first image is based on data from a first fluorescence imaging session, and a second image showing the visually enhanced attribute of the subject, wherein the second image is based on data from a second fluorescence imaging session, and determining a region of interest within the first image and the second image, generating metrics of the attribute of the subject within the region of interest for each of the first and second images, and updating the user interface to display the metrics.

In any of these embodiments, the region of interest within the first image may be determined based on an input by the user. In any of these embodiments, the input by the user may comprise insertion of a first bounding box on a portion of the user interface associated with the region of interest for the first image.

In any of these embodiments, the user interface may comprise a third image that is based on data from the first fluorescence imaging session, and the method may include automatically inserting a second bounding box on a portion of the user interface associated with the region of interest of the second image.

In any of these embodiments, the first and second images may comprise a maximum perfusion image or map, a maximum fluorescence intensity image or map, a coefficient-derived image or map, a fluorescence intensity variability image or map, an egress rate image or map, an ingress onset image or map, or a combination thereof.

In any of these embodiments, the first and second images may comprise color contrast. In any of these embodiments, the first and second images may comprise grayscale contrast. In any of these embodiments, the attribute may be an attribute of tissue of the subject.

According to some embodiments, a non-transitory computer readable storage medium storing one or more programs, the one or more programs comprising instructions, which when executed by an electronic system with a display, cause the system to perform a method comprising displaying a user interface on the display, the user interface comprising a first image showing a visually enhanced attribute of the subject, wherein the first image is based on data from a first fluorescence imaging session, and a second image showing the visually enhanced attribute of the subject, wherein the second image is based on data from a second fluorescence imaging session, and determining a region of interest within the first image and the second image, generating metrics of the attribute of the subject within the region of interest for each of the first and second images, and updating the user interface to display the metrics.

In any of these embodiments, the region of interest within the first image may be determined based on an input by the user. In any of these embodiments, the input by the user may comprise insertion of a first bounding box on a portion of the user interface associated with the region of interest for the first image.

In any of these embodiments, the user interface may comprise a third image that is based on data from the first fluorescence imaging session, and the one or more programs may include instructions for automatically inserting a second bounding box on a portion of the user interface associated with the region of interest of the second image.

In any of these embodiments, the first and second images may comprise a maximum perfusion image or map, a maximum fluorescence intensity image or map, a coefficient-derived image or map, a fluorescence intensity variability image or map, an egress rate image or map, an ingress onset image or map, or a combination thereof.

In any of these embodiments, the first and second images may comprise color contrast. In any of these embodiments, the first and second images may comprise grayscale contrast. In any of these embodiments, the attribute may be an attribute of tissue of the subject.

According to some embodiments, a system for displaying an attribute of a subject, the system comprising a display, one or more processors, memory, one or more programs stored in the memory and configured to be executed by the one or more processors, the one or more programs including instructions for displaying a user interface on the display, the user interface comprising a first image showing a visually enhanced attribute of the subject, wherein the first image is based on data from a fluorescence imaging session, determining a region of interest within the first image, generating metrics of the attribute of the subject within the region of interest, and updating the user interface to display the metrics.

In any of these embodiments, the region of interest within the first image may be determined based on an input by a user. In any of these embodiments, the input by the user may comprise insertion of a first bounding box on a portion of the user interface associated with the region of interest within the first image.

In any of these embodiments, the user interface may comprise a second image showing another visually enhanced attribute of the subject, wherein the second image is based on data from the fluorescence imaging session, and the one or more programs may include instructions for receiving a user input for selecting the second image, and in response to receiving the user input, replacing display of the first image with an enlarged second image.

In any of these embodiments, the one or more programs may include instructions for automatically determining a region of interest within the second image based on the region of interest within the first image.

In any of these embodiments, the first image may comprise a maximum perfusion image or map, a maximum fluorescence intensity image or map, a coefficient-derived image or map, a fluorescence intensity variability image or map, an egress rate image or map, an ingress onset image or map, or a combination thereof.

In any of these embodiments, the first and second images may comprise color contrast. In any of these embodiments, the first and second images may comprise grayscale contrast. In any of these embodiments, the attribute may be an attribute of tissue of the subject.

According to some embodiments, a method for displaying an attribute of a subject comprises, at a computer system comprising one or more processors, memory, and a display, displaying a user interface on the display, the user interface comprising a first image showing a visually enhanced attribute of the subject, wherein the first image is based on data from a fluorescence imaging session, determining a region of interest within the first image, generating metrics of the attribute of the subject within the region of interest, and updating the user interface to display the metrics.

In any of these embodiments, the region of interest within the first image may be determined based on an input by a user. In any of these embodiments, the input by the user may comprise insertion of a first bounding box on a portion of the user interface associated with the region of interest within the first image.

In any of these embodiments, the user interface may comprise a second image showing another visually enhanced attribute of the subject, wherein the second image is based on data from the fluorescence imaging session, and the method may include receiving a user input for selecting the second image, and in response to receiving the user input, replacing display of the first image with an enlarged second image.

In any of these embodiments, the method may include instructions for automatically determining a region of interest within the second image based on the region of interest within the first image.

In any of these embodiments, the first image may comprise a maximum perfusion image or map, a maximum fluorescence intensity image or map, a coefficient-derived image or map, a fluorescence intensity variability image or map, an egress rate image or map, an ingress onset image or map, or a combination thereof.

In any of these embodiments, the first and second images may comprise color contrast. In any of these embodiments, the first and second images may comprise grayscale contrast. In any of these embodiments, the attribute may be an attribute of tissue of the subject.

A non-transitory computer readable storage medium storing one or more programs, the one or more programs comprising instructions, which when executed by an electronic system with a display, cause the system to perform a method comprising displaying a user interface on the display, the user interface comprising a first image showing a visually enhanced attribute of the subject, wherein the first image is based on data from a fluorescence imaging session determining a region of interest within the first image, generating metrics of the attribute of the subject within the region of interest, and updating the user interface to display the metrics.

In any of these embodiments, the region of interest within the first image may be determined based on an input by a user. In any of these embodiments, the input by the user may comprise insertion of a first bounding box on a portion of the user interface associated with the region of interest within the first image.

In any of these embodiments, the user interface may comprise a second image showing another visually enhanced attribute of the subject, wherein the second image is based on data from the fluorescence imaging session, and the one or more programs may include instructions for receiving a user input for selecting the second image, and in response to receiving the user input, replacing display of the first image with an enlarged second image.

In any of these embodiments, the one or more programs may include instructions for automatically determining a region of interest within the second image based on the region of interest within the first image.

In any of these embodiments, the first image may comprise a maximum perfusion image or map, a maximum fluorescence intensity image or map, a coefficient-derived image or map, a fluorescence intensity variability image or map, an egress rate image or map, an ingress onset image or map, or a combination thereof.

In any of these embodiments, the first and second images may comprise color contrast. In any of these embodiments, the first and second images may comprise grayscale contrast. In any of these embodiments, the attribute may be an attribute of tissue of the subject.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 11 is a functional block diagram of a computing device according to an embodiment.

DETAILED DESCRIPTION

Reference will now be made in detail to implementations and embodiments of various aspects and variations of the invention, examples of which are illustrated in the accompanying drawings. Various medical imaging data management user interface systems and methods are described herein. Although at least two variations of user interface systems and methods are described, other variations of user interface systems and methods may include aspects of the systems and methods described herein combined in any suitable manner having combinations of all or some of the aspects described.

In accordance with one aspect of the invention, there is provided a system for management of data derived from medical imaging. The system comprises a display having a user interface, a control element operable by a user, a subject identifier element for identifying the subject (e.g., a patient or an animal), and a data view element for viewing the data derived from medical imaging, wherein the control element, the subject identifier element, and the data view element are configured to be displayed on the user interface, and wherein the data view element is configured to be displayed simultaneously for an initial assessment and one or more subsequent assessments following the initial assessment, or for two or more subsequent assessments following the initial assessment to facilitate an observation of a change in the tissue of a subject over time.

According to an embodiment, the various elements and actions that can be performed on the user interface are available in a single screen display. The system of the present invention supports quick decision-making by facilitating advanced analysis available with one click operation. Further analysis can be performed according to some embodiments, but is not necessary.

Figure 1:
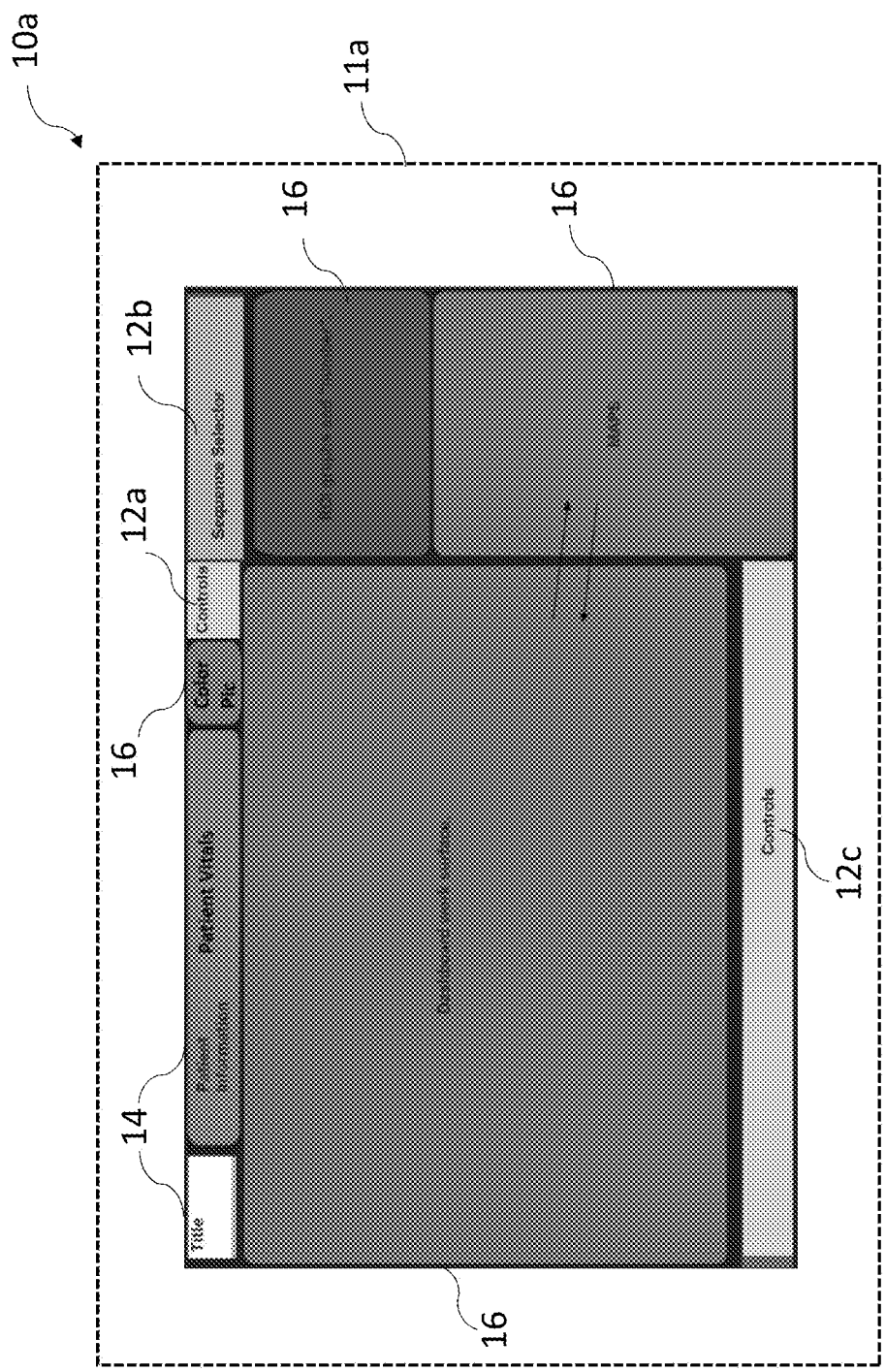
FIG. 1 illustrates a schematic example embodiment of a system for management of data derived from medical imaging, the system having a display comprising a user interface.

Referring to FIG. 1, there is provided a system 10a for management of data derived from medical imaging according to an embodiment. The system 10a comprises a display (not shown) having an analysis user interface 11a (e.g., a touch-screen user interface). As is illustrated in FIG. 1, the system 10a comprises one or more control element regions 12a-c in which control elements that are operable by a user may be included, a subject identifier element 14 for identifying the particulars of the subject, and a data view element 16 for viewing the data, which are displayed on the analysis user interface 11a. Examples of user interface 11a are provided in FIGS. 4A-5B.

One or more of the control element regions 12a-c include control elements operable by the user to facilitate selection of the information to be displayed. For example, in some embodiments, a zoom control is provided to facilitate zooming in and out of the displayed data view element 16. According to an embodiment, each adjustment of zoom may adjust the view such that only whole data view element 16 will be shown on the screen. A user can scroll up and down in the data view element 16 to access the desired information. In other embodiments, one or more control elements in regions 12a-c facilitate editing image data sequence information. In various other embodiments, one or more control elements facilitate moving or ordering data view elements 16 (e.g., rows of data view elements 16), where, for example, a row can be moved up or down.

The subject identifier element 14 for identifying the particulars of the subject facilitates entry of information such as, for example, the subject's name, gender, age, case name, assessment visit number, or a combination thereof.

In some embodiments, an anatomical view selector element (labeled "sequence selector" in user interface 11a) is included, for example in control element region 12b, to enable a user to navigate through different anatomical views of a subject. For example, a first view may be of the subject's foot (as shown in the examples of FIGS. 3A-5B) and a second view may be of the subject's knee and the sequence selector can include icons of the different views that the user may select to display the data associated with the selected view. The different anatomical views of a subject may also or alternatively include views from different angles of a particular anatomical location, for example a first view may be of the subject's foot as seen from a first angle and a second view may be of the subject's foot as seen from a second angle.

The data view elements 16 facilitate simultaneous viewing of various types of data derived from medical imaging over time (e.g., over the course of several assessment visits of the subject) on a single screen display (e.g., a mosaic or composite of various types of data derived from medical imaging concurrently displayed to the user). Examples of the data view elements 16 include a color image of the anatomy of the subject comprising the target tissue, a maximum perfusion (also referred to herein as maximum intensity) map or image of the tissue, a wound activity (also referred to herein as variability) map or image of the tissue, an egress rate map or image of the tissue, an ingress onset map or image of the tissue, a coefficient-derived map or image of the tissue (e.g., a venous coefficient-derived map/image or an arterial coefficient-derived map/image), other maps or visual representations derived from imaging data, a graphical representation of the various maps or images or of a region of interest in the maps or images, or a numeric representation of the various maps or images or of a region of interest in the maps or images (e.g., a quantifier such as a wound index value or variability index value) along with any annotations (e.g., descriptive text). Examples of such maps and other data are described in U.S. application Ser. No. 15/224,088 filed on Jul. 29, 2016, entitled "METHODS AND SYSTEMS FOR ASSESSING HEALING OF TISSUE" and U.S. application Ser. No. 15/013,945 filed on Feb. 2, 2016, entitled "METHODS AND SYSTEMS FOR CHARACTERIZING TISSUE OF A SUBJECT" which are incorporated by reference in their entireties.

In the context of this specification, a "color image" of the anatomy of the subject refers to a white-light image or photograph of the anatomy of the subject.

A "maximum perfusion" map or image (also referred to herein as "maximum intensity"), such as a fluorescence maximum perfusion map or image, refers to a map or image created by assigning each pixel in the calculation region of the time series of fluorescence input images the value of its maximum intensity reached during the entire measurement period (where the calculation region may be a single pixel or a group of pixels or a voxel or a group of voxels, or some other spatially defined area or volume in the time series of fluorescence images).

A "wound activity" map or image (also referred to as "variability") refers to a map or image that is generated from a plurality of visualized ranked time-intensity curves for a calculation region in a time series of input data obtained from the target tissue (e.g., fluorescence image input data), where the time series of input data captures the transit of an imaging agent through the target tissue. Perfusion dynamics for every pixel in a selected calculation region of an image (i.e., a region of interest for which to perform the ranking analysis) in a time series of fluorescence input images can be characterized by the shape of its time-intensity curve. The curves can be classified based on some pre-defined criteria, and as a result, every pixel can be assigned a "rank" corresponding to the type of curve it exhibits.

An "egress rate" map or image (also referred to herein as "venous") refers to a map or image generated from the time point when a certain intensity is reached at a point compared to its maximum intensity.

A "coefficient-derived" image is obtained by using a mathematical model approximating a signal intensity arising from an imaging agent circulating with blood and transiting vasculature of the tissue as a function of time. A coefficient for the mathematical model is calculated at one or more points on the tissue using empirical signal intensity data for the imaging agent in the tissue (the empirical signal intensity data includes a set of intensity values over time). A plurality of the calculated coefficients is subsequently used to generate a coefficient-derived image of the tissue (e.g., by assigning a pixel intensity to each coefficient), where a difference in the coefficients correlates with a difference in dynamics of the imaging agent in the tissue. Examples of the coefficient-derived image include an arterial coefficient-derived image generated from influx coefficients, and a venous coefficient-derived image generated from efflux coefficients.

A "wound index" value (also referred to herein as a "variability index" value) is generated by comparing each of the rank values in the wound activity or variability map/image with a reference value, and provides a quantification tool for tracking the wound and the wound treatment progress.

The various maps or images may be either colorized or grayscale, depending on user selection using the control elements in control element regions 12a-c, and may have one or more regions of interest shown on them, if the user has chosen to use the region of interest feature. In some embodiments, the maximum perfusion maps or images may have relative markers, if the user has chosen to use such a feature. Furthermore, in various embodiments, the maps or images of the tissue, and the color image of the anatomy may have annotations, if user has chosen to annotate such maps/images or the color image. In various other embodiments, a reference may be selected for a particular region of interest in the maps or images of the tissue.

According to an embodiment, the data view element 16 from an initial assessment visit ("assessment visit" is used interchangeably herein with "encounter" and "imaging session") or a plurality of the data view elements 16 from an initial assessment visit in combination with one or more subsequent assessment visits, for example, are immediately displayed on the user interface upon the user initiating access to the particular subject's data from the previous assessment. Such a display capability facilitates ensuring that users consistently acquire acquisitions with generally the same anatomical view and camera set up over multiple assessment visits, and facilitates providing an ordered sequential workflow to ensure consistent sequence and white-light (color) image assessment. Upon uploading one or more data view elements 16 of the previous visit, the user then can acquire and immediately display in real time or after a short delay (e.g., in the order of a few seconds) the data view element 16 of the current assessment visit for immediate review and assessment of the case over time (e.g., over multiple assessment visits or multiple cases). A report can be generated with the desired information present in the report and printed and/or exported as an image file following an assessment visit for example. According to an embodiment, the report may have one or more of the control elements in one or more control element regions 12a-c (or the entire control regions) removed.

Figure 2:
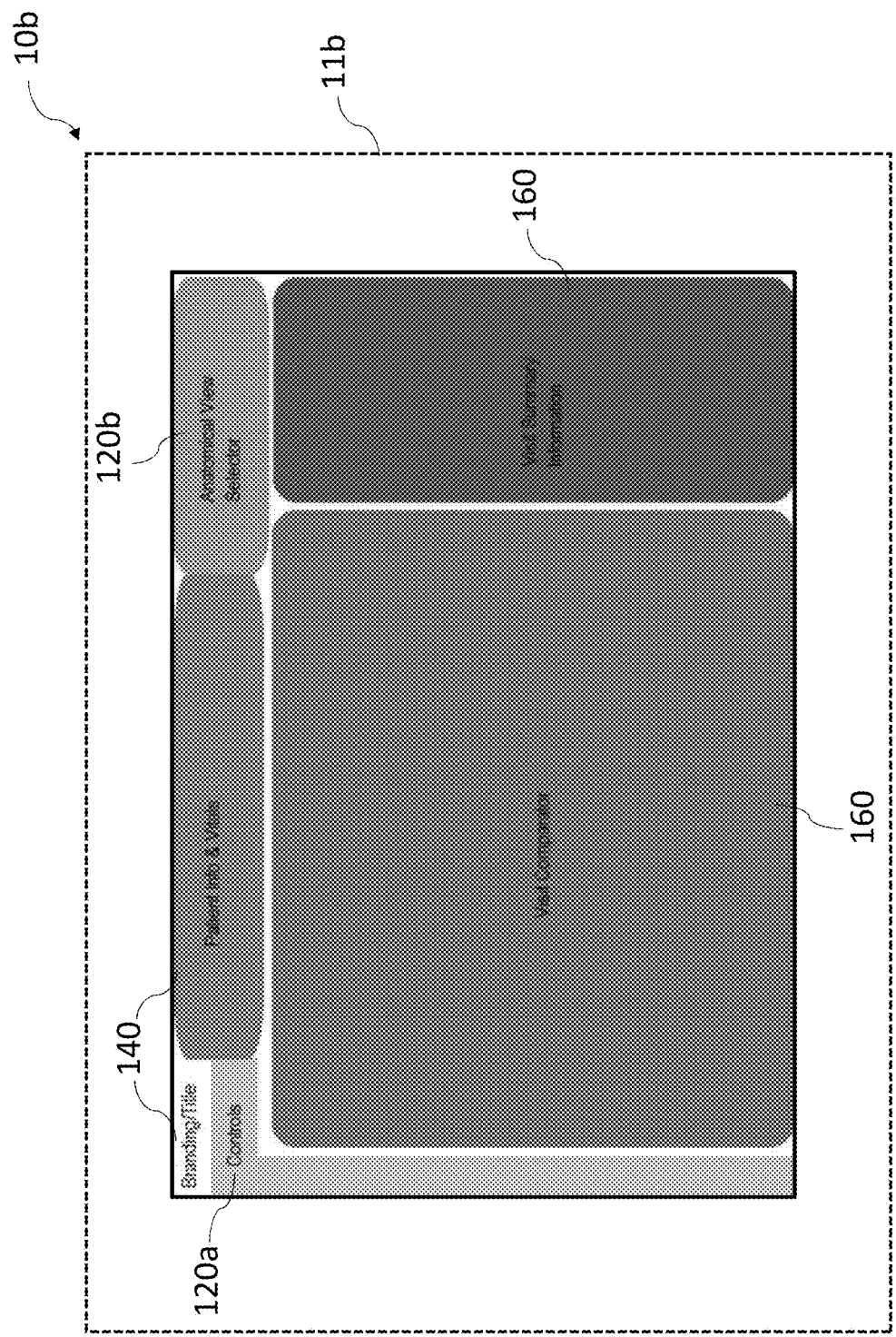
FIG. 2 illustrates a schematic example embodiment of a system for management of data derived from medical imaging, the system having a display comprising a user interface.

FIG. 2 illustrates a system 10b for management of data derived from medical imaging of a subject according to an embodiment. In this embodiment, case management user interface 11b includes one or more data view elements 160 for displaying attributes (characteristics) of the subject based on the data derived from the medical imaging of the subject. In some embodiments, a data view element 160 may be a visit comparator that includes a plurality of data views from several assessment visits of the subject. Attributes of the subject (e.g., tissue of an anatomical portion of the subject) may be simultaneously or concurrently compared by displaying various data view elements 160 on a single screen for each assessment visit as a matrix, and immediately comparing the data view elements 160 obtained in real time with such previously acquired data view elements 160. Examples of case management user interface 11b are included in FIGS. 3A-3C.

A skilled person will appreciate that in some embodiments, the system for management of data derived from medical imaging (e.g., the system 10a or 10b) is a stand-alone system, while in other embodiments, the system may be a component of an imaging system for acquiring the data derived from medical imaging (e.g., a fluorescence imaging system).

In various embodiments, the systems and methods for management of data derived from medical imaging facilitate consistent acquisition of medical imaging data or data derived from medical imaging with generally similar anatomical view and positioning over multiple assessment visits of the subject. In further embodiments, the systems and methods for management of data derived from medical imaging facilitate an ordered sequential workflow to ensure consistent image data sequence and white-light image assessment. In further embodiments, the systems and methods for management of data derived from medical imaging help to reduce the opportunity for the operator to create "orphaned" images and image data sequences, which cannot be used for analysis and assessment. In further embodiments, the systems and methods for management of data derived from medical imaging facilitate ease of review and comparison of multiple cases, including analyses over time (e.g., side-by-side). The systems and methods further facilitate, in various embodiments, associating subject assessment visits with clinical cases in order and in which serial case histories can be easily managed and assessed. In various other embodiments, the systems and methods provide the ability for an operator to hide confidential information from subjects during a clinical case, filter subject assessment visits to enhance nurse workflow to complete subject records, print/export reports and archive/export data off the system, and/or update reporting feature to become more flexible and with the information.

According to yet another aspect of the invention there is provided a tangible non-transitory computer readable medium having computer-executable (readable) program code means embedded thereon comprising the method for management of data derived from medical imaging as described above.

In yet further aspects, there is provided a kit including a medical imaging system (e.g., a fluorescence medical imaging system) and an imaging agent (e.g., a fluorescence imaging agent, for example, a fluorescence dye such as ICG or methylene blue) wherein the medical imaging system is configured to perform the method for management of data derived from medical imaging or wherein the medical imaging system is in communication with the system for management of data derived from medical imaging as described in connection with the various embodiments.

One skilled in the art will appreciate that although the various exemplary embodiments are illustrated in the Examples section of the specification and FIGS. 3 to 8, with image data management in the context of fluorescence image data, the systems and methods may be applied to other medical imaging applications, including for example, medical imaging applications employing radiographic imaging or contrast agents.

EXAMPLES

Use of the System for Image Data Management with a Fluorescence Medical Imaging System for Acquiring Fluorescence Medical Imaging Data According to one aspect of the invention, a system for management of data derived from medical imaging may be used with or as a component of a medical imaging system such as, for example, a fluorescence medical imaging system for acquiring fluorescence medical imaging data. An example of such a fluorescence medical imaging system is the fluorescence imaging system 20 schematically illustrated in FIG. 6. In this embodiment, the fluorescence imaging system 20 is configured to acquire a time series of signal intensity data (e.g., images) capturing the transit of a fluorescence imaging agent through the tissue.

The fluorescence imaging system 20 (FIG. 6) comprises a light source 22 to illuminate the tissue of the subject to induce fluorescence emission from a fluorescence imaging agent 24 in the tissue of the subject (e.g., in blood), an image acquisition assembly 26 configured to acquire the time series of fluorescence images from the fluorescence emission, and a processor assembly 28 configured to utilize the acquired time series of fluorescence images (fluorescence signal intensity data) according to the various embodiments of the present invention.

In various embodiments, the light source 22 (FIG. 6) comprises, for example, an illumination module 30 (FIG. 7) comprising a fluorescence excitation source configured to generate an excitation light having a suitable intensity and a suitable wavelength for exciting the fluorescence imaging agent 24. FIG. 7 shows an example illumination module 30 according to an embodiment. The illumination module 30 comprises a laser diode 32 (e.g., which may comprise, for example, one or more fiber-coupled diode lasers) configured to provide an excitation light to excite the fluorescence imaging agent 24 (not shown). Examples of other sources of the excitation light which may be used in various embodiments include one or more LEDs, arc lamps, or other illuminant technologies of sufficient intensity and appropriate wavelength to excite the fluorescence imaging agent 24 in the tissue (e.g., in blood). For example, excitation of the fluorescence imaging agent 24 in blood, wherein the fluorescence imaging agent 24 is a fluorescence dye with near infra-red excitation and emission characteristics, may be performed using one or more 793 nm, conduction-cooled, single bar, fiber-coupled laser diode modules from DILAS Diode Laser Co, Germany.

Figure 6:
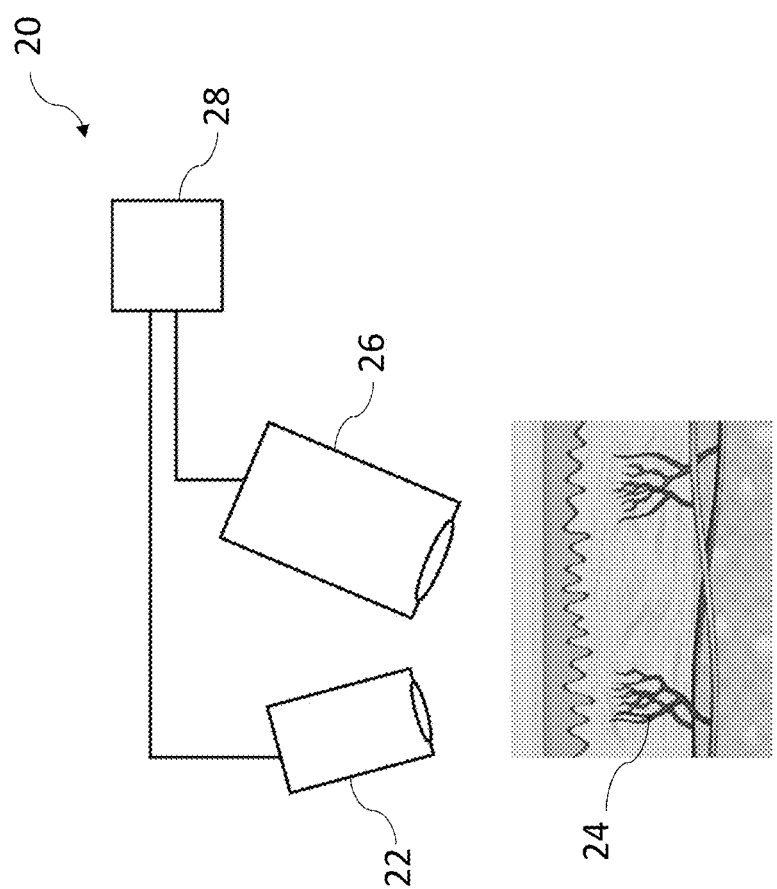
FIG. 6. schematically illustrates an example fluorescence imaging system for use in acquiring data derived from fluorescence medical imaging.
Figure 7:
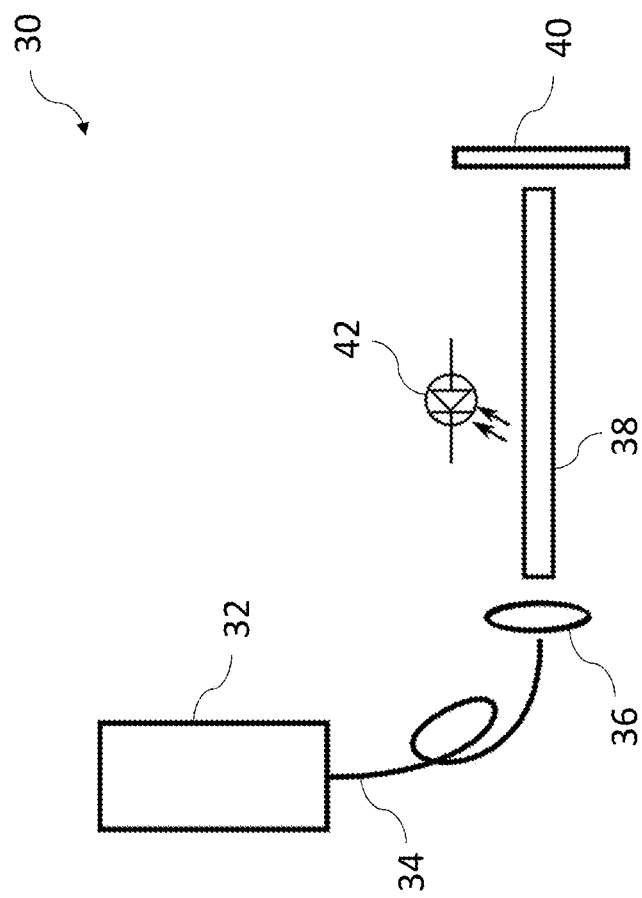
FIG. 7 illustrates an example illumination module of the fluorescence imaging system according to an embodiment.

In various embodiments, the light output from the light source 22 in FIG. 6 may be projected through an optical element (i.e., one or more optical elements) to shape and guide the output being used to illuminate the tissue area of interest. The shaping optics may consist of one or more lenses, light guides, and/or diffractive elements so as to ensure a flat field over substantially the entire field of view of the image acquisition assembly 26. In particular embodiments, the fluorescence excitation source is selected to emit at a wavelength close to the absorption maximum of the fluorescence imaging agent 24 (e.g., ICG). For example, referring to the embodiment of the illumination module 30 in FIG. 7, the output 34 from the laser diode 32 is passed through one or more focusing lenses 36, and then through a homogenizing light pipe 38 such as, for example, light pipes commonly available from Newport Corporation, USA. Finally, the light is passed through an optical diffractive element 40 (i.e., one or more optical diffusers) such as, for example, ground glass diffractive elements also available from Newport Corporation, USA. Power to the laser diode 32 itself is provided by, for example, a high-current laser driver such as those available from Lumina Power Inc. USA. The laser may optionally be operated in a pulsed mode during the image acquisition process. In this embodiment, an optical sensor such as a solid state photodiode 42 is incorporated into the illumination module 30 and samples the illumination intensity produced by the illumination module 30 via scattered or diffuse reflections from the various optical elements. In various embodiments, additional illumination sources may be used to provide guidance when aligning and positioning the module over the area of interest.

Figure 8:
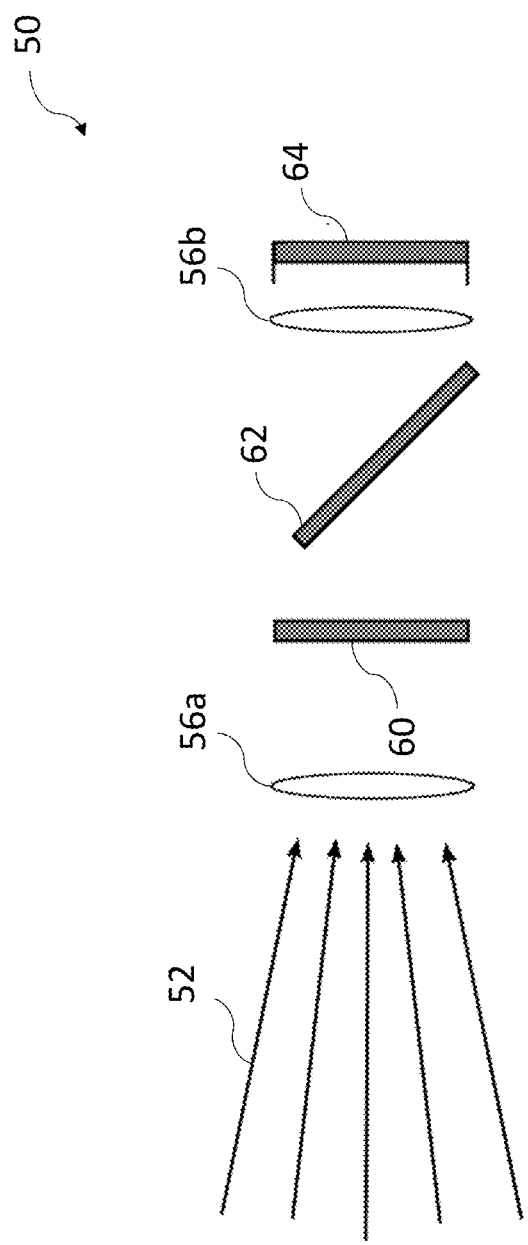
FIG. 8 illustrates an example camera module of the fluorescence imaging system according to an embodiment.

Referring back to FIG. 6, in various embodiments, the image acquisition assembly 26 may be a component of, for example, the fluorescence imaging system 20 configured to acquire the time series of fluorescence images from the fluorescence emission from the fluorescence imaging agent 24. Referring to FIG. 8, there is shown an exemplary embodiment of an image acquisition assembly 26 comprising a camera module 50. As is shown in FIG. 8, the camera module 50 acquires images of the fluorescence emission 52 from the fluorescence imaging agent 24 in the tissue (e.g., in blood) (not shown) by using a system of imaging optics (e.g., 56a, 56b, 60 and 62) to collect and focus the fluorescence emission onto an image sensor assembly 64 comprising at least one 2D solid state image sensor. The solid state image sensor may be a charge coupled device (CCD), a CMOS sensor, a CID or similar 2D sensor technology. The charge that results from the optical signal transduced by the image sensor assembly 64 is converted to an electrical video signal, which includes both digital and analog video signals, by the appropriate read-out and amplification electronics in the camera module 50.

According to an embodiment, an excitation wavelength of about 800 nm+/−10 nm and emission wavelengths of >820 nm are used along with NIR compatible optics for ICG fluorescence imaging. A skilled person will appreciate that other excitation and emission wavelengths are used for other imaging agents.

Referring back to FIG. 6, in various embodiments, the processor assembly 28 comprises, for example,
- a processor module (not shown) configured to perform various processing operations, and
- a data storage module (not shown) to record the data from the operations.

In various embodiments, the processor module comprises any computer or computing means such as, for example, a tablet, laptop, desktop, networked computer, or dedicated standalone microprocessor. Inputs are taken, for example, from the image sensor 64 of the camera module 50 shown in FIG. 8, from the solid state photodiode in the illumination module 30 in FIG. 7, and from any external control hardware such as a footswitch or remote-control. Output is provided to the laser diode driver and optical alignment aids. In various embodiments, the processor assembly 28 (FIG. 6) may have a data storage module with the capability to save the time series of input data (e.g., image data) to a tangible non-transitory computer readable medium such as, for example, internal memory (e.g. a hard disk or flash memory), so as to enable recording and processing of data. In various embodiments, the processor module may have an internal clock to enable control of the various elements and ensure correct timing of illumination and sensor shutters. In various other embodiments, the processor module may also provide user input and graphical display of outputs. The fluorescence imaging system may optionally be configured with a video display (not shown) to display the images as they are being acquired or played back after recording, or further to visualize the data generated at various stages of the method as was described above.

In operation, and with continuing reference to the exemplary embodiments in FIGS. 6 to 8, the subject is positioned such that an area of interest is located beneath both the light source 22, and the image acquisition assembly 26 such that a substantially uniform field of illumination is produced across substantially the entire area of interest. In various embodiments, prior to the administration of the fluorescence imaging agent 24 to the subject, an image may be acquired of the area of interest for the purposes of background deduction. For example, in order to do this, the operator of the fluorescence imaging system 20 in FIG. 6 may initiate the acquisition of the time series of fluorescence images by depressing a remote switch or foot-control, or via a keyboard (not shown) connected to the processor assembly 28. As a result, the light source 22 is turned on and the processor assembly 28 begins recording the fluorescence image data provided by the image acquisition assembly 26. In lieu of the pulsed mode, it will be understood that in some embodiments, the light source 22 can comprise an emission source which is continuously on during the image acquisition sequence. When operating in the pulsed mode of the embodiment, the image sensor 64 in the camera module 50 is synchronized to collect fluorescence emission following the laser pulse produced by the diode laser 32 in the illumination module 30. In this way, maximum fluorescence emission intensity is recorded, and signal-to-noise ratio is optimized. In this embodiment, the fluorescence imaging agent 24 is administered to the subject and delivered to the area of interest via arterial flow. Acquisition of the time series of fluorescence images is initiated, for example, shortly after administration of the fluorescence imaging agent 24, and the time series of fluorescence images from substantially the entire area of interest are acquired throughout the ingress of the fluorescence imaging agent 24. The fluorescence emission from the region of interest is collected by the collection optics of the camera module 50. Residual ambient and reflected excitation light is attenuated by subsequent optical elements (e.g., optical element 60 in FIG. 8 which may be a filter) in the camera module 50 so that the fluorescence emission can be acquired by the image sensor assembly 64 with minimal interference by light from other sources.

In various embodiments, the processor is in communication with the imaging system or is a component of the imaging system. An example of the imaging system is the fluorescence imaging system described above, however, a skilled person will appreciate that other imaging systems may be used depending on the type of imaging being performed.

In some embodiments, a time series of fluorescence images comprises a plurality of individual image frames (e.g., fluorescence image frames), or data representative of individual frames, ordered consecutively by acquisition time. The fluorescence images may subsequently also stored as a series of individual frames, or data representative of individual frames (e.g., compressed video), ordered consecutively by their acquisition time.

In some embodiments, the individual image frames of the time series are spatially aligned or registered. For example, a typical time series of fluorescence images may be recorded over 2 to 3 minutes, during which some subject's movements may be unavoidable. As a result, the same anatomical features can appear at different positions in image frames acquired at different times during the image time series acquisition period. Such misalignments can introduce errors in the subsequent analysis where the level of fluorescence for each pixel or a group of pixels is followed over time. To help reduce errors, the generated image frames may be spatially aligned (registered) with each other. In some embodiments, image registration or alignment refers to a process of determining the spatial transform that maps points from one image to homologous points in the second image.

Image registration may be an iterative process. For example, according to an exemplary embodiment, image registration may use one or more of the following set of components: two input images, a transform, a metric, an interpolator, and an optimizer. A transform maps the fixed image space into the moving image space. An optimizer is required to explore the parameter space. An Insight Segmentation and Registration Toolkit (ITK) (http://itk.org/) based implementation of the transform in search of optimal values of the metric may be used. The metric compares how well the two images match each other. Finally, the interpolator evaluates the intensities of the moving image at non-grid positions. To align the entire time series of fluorescence images, this procedure is executed for all the frames included in the analysis. The component loops through the range of input series frames, subtracts a background image for baseline correction and applies noise-reduction filters, then registers consecutive pairs of images.

In some embodiments, the data for a plurality of time series of fluorescence images and/or the subject time series of fluorescence images, which includes image data, may comprise raw data, preprocessed data, or a combination thereof. In some embodiments, the time series of fluorescence images and/or the subject time series of fluorescence images is pre-processed to, for example, extract selected data, calculate a baseline intensity, perform an image quality improvement process, or a combination thereof.

Extraction of selected data may, for example, comprise cropping to locate and exclude certain data from the image time series data. For example, during a fluorescence imaging procedure of the subject, an operator might start recording the time series of fluorescence images and/or the subject time series of fluorescence images well before the fluorescence imaging agent reaches the target tissue As a result, the time series of fluorescence images might have a significant number of "dark" frames in the beginning, thus adding unnecessary computational time for the frames that contain no meaningful data. To mitigate the problem, cropping can be used to remove those "dark" frames from the beginning of the time series of fluorescence images. In addition, when the subject is injected with the fluorescence imaging agent (e.g., ICG), the fluorescence signal from the imaging agent as it transits the target tissue typically proceeds through a series of phases: rapid increase of fluorescence intensity as the imaging agent enters the tissue through arterial vessels, followed by a period of stable fluorescence as the imaging agent traverses the microvasculature, then slow decrease in fluorescence intensity due to the venous outflow of the imaging agent, followed by a period of residual fluorescence as any imaging agent retained in the lining of the vasculature released into the bloodstream. This last "residual" phase can last for several minutes and, as it is not directly indicative of blood flow, does not typically provide meaningful perfusion information. Thus, cropping may be used to locate and exclude the residual phase from subsequent steps of analysis.

In some embodiments, pre-processing may include calculation of the baseline intensity. For example, when the time series of fluorescence images and/or the subject time series of fluorescence images is being generated by a fluorescence imaging system, various external factors can contribute to the fluorescence of the recorded series, such as camera noise, thermal noise, and/or presence of residual fluorescence dye from an earlier injection. In order to minimize the influence of such factors on the analysis, the baseline intensity may be calculated for every series, and the analysis of the data may be adjusted accordingly.

In some embodiments, pre-processing may include an image quality validation process. Such a process may comprise a starting brightness test in embodiments where, for example, the acquisition of the time series of fluorescence images has started too late and the imaging agent has already begun its transit of the target tissue by the time the first frame was captured. In this scenario, the time series of fluorescence images cannot be reliably analyzed or processed since the information relating to the start of perfusion has been lost. As a result, such series data would be rejected.

In some embodiments, the image quality validation process may comprise a brightness change test. Such a test may be used, for example, in instances where the fluorescence imaging system was suddenly moved during the image acquisition, foreign objects appeared in the field of view, or a light from an external source illuminated the scene while the series was being captured. All of these events may significantly distort the results of any subsequent analysis. Accordingly, the time series of fluorescence images subjected to such a test might fail the validation procedure (be identified as being unsuitable for further processing). According to an exemplary embodiment, the brightness change test comprises a calculation of the difference between average intensities of neighboring frames in the time series of fluorescence images and compares it to a selected intensity difference threshold. In order to pass validation, the differences in intensities of all consecutive frames must be within the limit specified by the selected intensity difference threshold.

In some embodiments, the image quality validation process may comprise an intensity peak location test to check that the acquisition of the time series of fluorescence images has not been stopped prematurely. For example, the intensity peak location test ensures that a sufficient number of frames have been acquired to cover all phases of the dye bolus transit through the tissue. According to an exemplary embodiment, the fluorescence intensity peak location test comprises finding the frame with the maximum average fluorescence intensity and verifying that it is not the last frame in the time series of fluorescence images. Should this condition fail, it will be a strong indication that the fluorescence intensity values have not reached their maximum yet and such a time series of fluorescence images is not suitable for further analysis.

In some embodiments, the image quality validation process may yet further comprise a maximum fluorescence intensity test. The purpose of the test is to filter out the time series of fluorescence images in which the images are too dark (majority of pixels fall below a pre-defined threshold) or over-saturated (majority of pixels are above a pre-defined saturation threshold).

The curvature of the tissue surface, excessive movement during the image acquisition procedure, dark or oversaturated images, foreign objects within imaged area and external light or shading can affect the quality of the time series of fluorescence images and/or the subject time series of fluorescence images, and thus the subsequent processing of such image data. To mitigate these problems, a well-structured imaging protocol and a fluorescence imaging system designed to minimize such issues may be used.

The preprocessing may vary depending on the type of data and/or imaging application.

One skilled in the art will appreciate that program code means according to the various embodiments can be written in any appropriate programming language and delivered to the processor in many forms, including, for example, but not limited to information permanently stored on non-writeable storage media (e.g., read-only memory devices such as ROMs or CD-ROM disks), information alterably stored on writeable storage media (e.g., hard drives), information conveyed to the processor through communication media, such as a local area network, a public network such as the Internet, or any type of media suitable for storing electronic instruction. When carrying computer readable instructions that implement the various embodiments of the method of the present invention, such computer readable media represent examples of various embodiments of the present invention. In various embodiments, the tangible non-transitory computer readable medium comprises all computer-readable media, and the present invention scope is limited to computer readable media wherein the media is both tangible and non-transitory.

In an embodiment, the system and method for management of data derived from medical imaging may be a component of the medical imaging system such as the fluorescence medical imaging system 20, which acquires the medical imaging data and is further configured to generate the various data view elements 16 as was described above.

Example Imaging Agents for Use in Generating Medical Imaging Data

According to an embodiment, in fluorescence medical imaging applications, the imaging agent is a fluorescence imaging agent such as, for example, indocyanine green (ICG) dye. ICG, when administered to the subject, binds with blood proteins and circulates with the blood in the tissue. The fluorescence imaging agent (e.g., ICG) may be administered to the subject as a bolus injection (e.g., into a vein or an artery) in a concentration suitable for imaging such that the bolus circulates in the vasculature and traverses the microvasculature. In other embodiments in which multiple fluorescence imaging agents are used, such agents may be administered simultaneously, e.g. in a single bolus, or sequentially in separate boluses. In some embodiments, the fluorescence imaging agent may be administered by a catheter. In certain embodiments, the fluorescence imaging agent may be administered less than an hour in advance of performing the measurement of signal intensity arising from the fluorescence imaging agent. For example, the fluorescence imaging agent may be administered to the subject less than 30 minutes in advance of the measurement. In yet other embodiments, the fluorescence imaging agent may be administered at least 30 seconds in advance of performing the measurement. In still other embodiments, the fluorescence imaging agent may be administered contemporaneously with performing the measurement.

According to an embodiment, the fluorescence imaging agent may be administered in various concentrations to achieve a desired circulating concentration in the blood. For example, in embodiments where the fluorescence imaging agent is ICG, it may be administered at a concentration of about 2.5 mg/mL to achieve a circulating concentration of about 5 µM to about 10 µM in blood. In various embodiments, the upper concentration limit for the administration of the fluorescence imaging agent is the concentration at which the fluorescence imaging agent becomes clinically toxic in circulating blood, and the lower concentration limit is the instrumental limit for acquiring the signal intensity data arising from the fluorescence imaging agent circulating with blood to detect the fluorescence imaging agent. In various other embodiments, the upper concentration limit for the administration of the fluorescence imaging agent is the concentration at which the fluorescence imaging agent becomes self-quenching. For example, the circulating concentration of ICG may range from about 2 µM to about 10 mM. Thus, in one aspect, the method comprises the step of administration of the imaging agent (e.g., a fluorescence imaging agent) to the subject and acquisition of the signal intensity data prior to processing the signal intensity data according to the various embodiments. In another aspect, the method excludes any step of administering the imaging agent to the subject.

A suitable fluorescence imaging agent for use in fluorescence imaging applications to generate fluorescence imaging data is an imaging agent which can circulate with the blood (e.g., a fluorescence dye which can circulate with, for example, a component of the blood such as lipoproteins or serum plasma in the blood) and transit vasculature of the tissue (i.e., large vessels and microvasculature), and from which a signal intensity arises when the imaging agent is exposed to appropriate light energy (e.g., excitation light energy, or absorption light energy). In various embodiments, the fluorescence imaging agent comprises a fluorescence dye, an analogue thereof, a derivative thereof, or a combination of these. A fluorescence dye includes any non-toxic fluorescence dye. In certain embodiments, the fluorescence dye optimally emits fluorescence in the near-infrared spectrum. In certain embodiments, the fluorescence dye is or comprises a tricarbocyanine dye. In certain embodiments, the fluorescence dye is or comprises indocyanine green (ICG), methylene blue, or a combination thereof. In other embodiments, the fluorescence dye is or comprises fluorescein isothiocyanate, rhodamine, phycoerythrin, phycocyanin, allophycocyanin, o-phthaldehyde, fluorescamine, rose Bengal, trypan blue, fluoro-gold, or a combination thereof, excitable using excitation light wavelengths appropriate to each dye. In some embodiments, an analogue or a derivative of the fluorescence dye may be used. For example, a fluorescence dye analog or a derivative includes a fluorescence dye that has been chemically modified, but still retains its ability to fluoresce when exposed to light energy of an appropriate wavelength.

In various embodiments, the fluorescence imaging agent may be provided as a lyophilized powder, solid, or liquid. In certain embodiments, the fluorescence imaging agent may be provided in a vial (e.g., a sterile vial), which may permit reconstitution to a suitable concentration by administering a sterile fluid with a sterile syringe. Reconstitution may be performed using any appropriate carrier or diluent. For example, the fluorescence imaging agent may be reconstituted with an aqueous diluent immediately before administration. In various embodiments, any diluent or carrier which will maintain the fluorescence imaging agent in solution may be used. As an example, ICG may be reconstituted with water. In some embodiments, once the fluorescence imaging agent is reconstituted, it may be mixed with additional diluents and carriers. In some embodiments, the fluorescence imaging agent may be conjugated to another molecule, e.g., a protein, a peptide, an amino acid, a synthetic polymer, or a sugar e.g., to enhance solubility, stability, imaging properties or a combination thereof. Additional buffering agents may optionally be added including Tris, HCl, NaOH, phosphate buffer, HEPES.

One skilled in the art will appreciate that although a fluorescence imaging agent was described above in detail, other imaging agents depending on the medical imaging technique. An example of such an imaging agent may be a radiographic imaging or contrast agent.

Examples of Image Data Management According to Various Embodiments

FIGS. 3A to 5B illustrate exemplary user interfaces and exemplary clinical results generated according to the various embodiments described above relating to an application of the methods and systems to image data management of fluorescence image data of a tissue of a subject. The fluorescence image data was generated using a fluorescence imaging system (available from NOVADAQ® Technologies Inc.), and ICG was used as the fluorescence imaging agent.

Figure 3A:
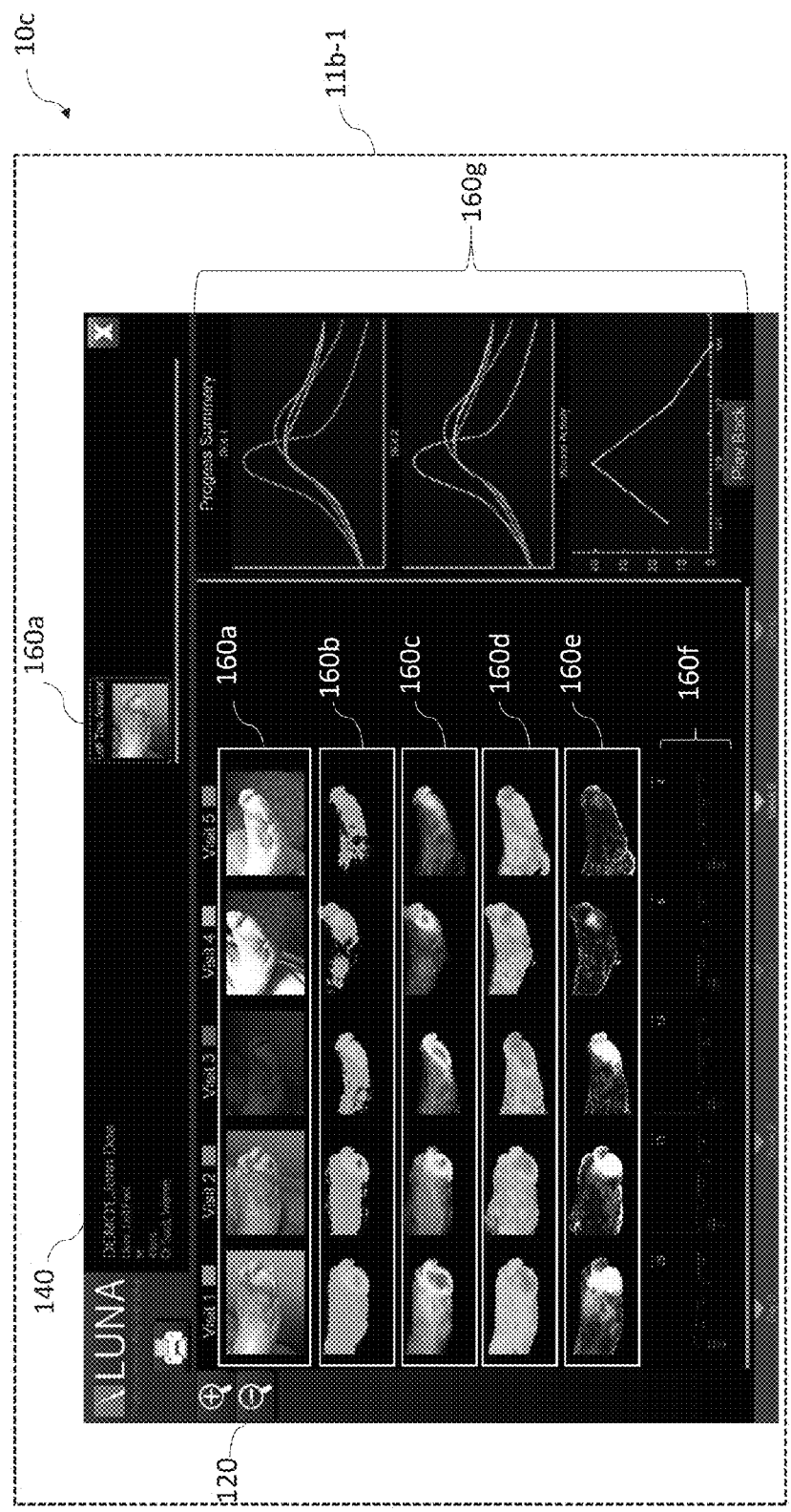
FIG. 3A illustrates example clinical image data generated by a fluorescence imaging system, and management of such data derived from fluorescence imaging according to an embodiment.

FIG. 3A illustrates image data management user interface 11b-1 according to an embodiment where the various data view elements 160 (i.e., 160a, 160b, 160c, 160d, 160e, 160f, and 160g) are simultaneously displayed to the user on the user interface 11b-1 over a number of assessment visits (e.g., visits 1 through 5). For example, data view elements 160a illustrate a series of color images for each of the assessment visits, data view elements 160b illustrate the corresponding wound activity (variability) maps or images, data view elements 160c illustrate the corresponding maximum perfusion (maximum intensity) maps or images, data view elements 160d illustrate the corresponding egress rate maps or images, and data view elements 160e illustrate the corresponding coefficient-derived maps or images (i.e., the venous coefficient-derived maps or images).

Numerical and graphical data in connection with one or more of the data view elements 160b, 160c, 160d, and 160e can be simultaneously presented as is illustrated in data view elements 160f and 160g. For example, data view element 160f includes a graph of wound index (quantifier) for each of the respective assessment visits. The wound index graph for the Day 0 assessment visit included in data view element 160f is shown in enlarged form in FIG. 4A.

In the example of FIG. 3A, data view element 160g includes three graphs representing aspects of the fluorescence imaging derived data. The top two graphs provide intensity as a function of time within a region of interest for each of the assessment visits. The bottom graph illustrates wound activity across the assessment visits. These particular graphs are provided for illustration only. Data view element 160g can include any other information that may be of interest to a user, including, for example, textual and numerical information.

Figure 3B:
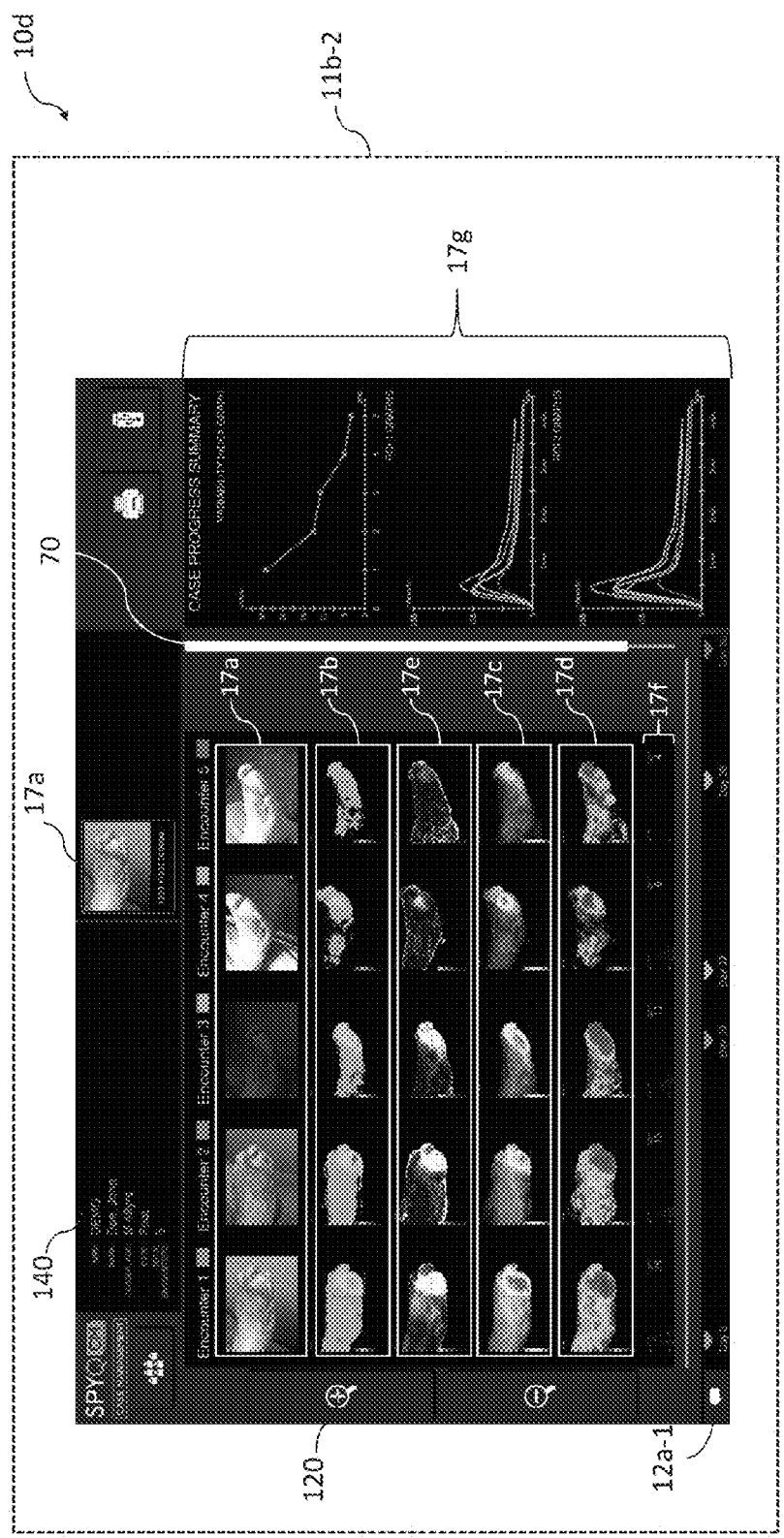
FIG. 3B illustrates example clinical image data generated by a fluorescence imaging system, and management of such data derived from fluorescence imaging according to an embodiment.

FIG. 3B illustrates another embodiment of an image data management user interface 11b-2. Relative to the user interface of FIG. 3A, the ordering of some of the data view elements is shifted. In some embodiments, the ordering of data view elements is user configurable, for example, to enable a user to position a data view element of particular interest in a more prominent position, or to enable a user to compare particular data view elements more closely by arranging them near to each other. User interface 11b includes scroll bar 70 to enable scrolling of the data view elements. This can allow larger data view elements to be included without reducing the number of data view elements available. For example, as shown in FIG. 3B, data view elements 16f are partially hidden but can be fully displayed by scrolling the data view elements up using scroll bar 70. A scroll bar, such as a horizontal scroll bar, can be included to scroll across the assessment visits if there is insufficient space to accommodate all the assessment visits.

FIG. 3B also includes zoom controls in control element region 120 (as shown in user interface 11b of FIG. 2). User selection of the zoom controls can zoom in and out on the data view elements. Upon reaching a zoom level in which not all data view elements 16 can be simultaneously accommodated on the user interface, one or more scrolls bars may appear or become active. In some embodiments, a user can pan the data view elements 16, for example, using a drag touch gesture or a click and drag gesture. The embodiments of FIG. 3B illustrates a default zoom level in which the data view elements 17f are partially hidden, but still show the "variability" measure for the respective visits (e.g., "29" for Encounter 1, "15" for Encounter 2), values that are also represented in the top graph of data view element 17g in the embodiments of FIG. 3B.

In the example of FIG. 3B, color scales are provided for each of the data view elements. Color scales may be identical within a given data view element across the encounters. The color scale may be defined based data within a single encounter or based on data of several encounters. For example, a color scale may be defined by determining the maximum range of intensity values across several encounters and using the maximum range for as the minimum and maximum of the scale. In other embodiments, the scale may be determined based on, for example, a minimum intensity value or an average intensity value across all the encounter data. The determined scale is then used to determine the coloring for each of the same types of images. In some embodiments, the scale is determined based on only the values for a single encounter (e.g., the first encounter) and the color scale is applied across all encounters.

Figure 3C:
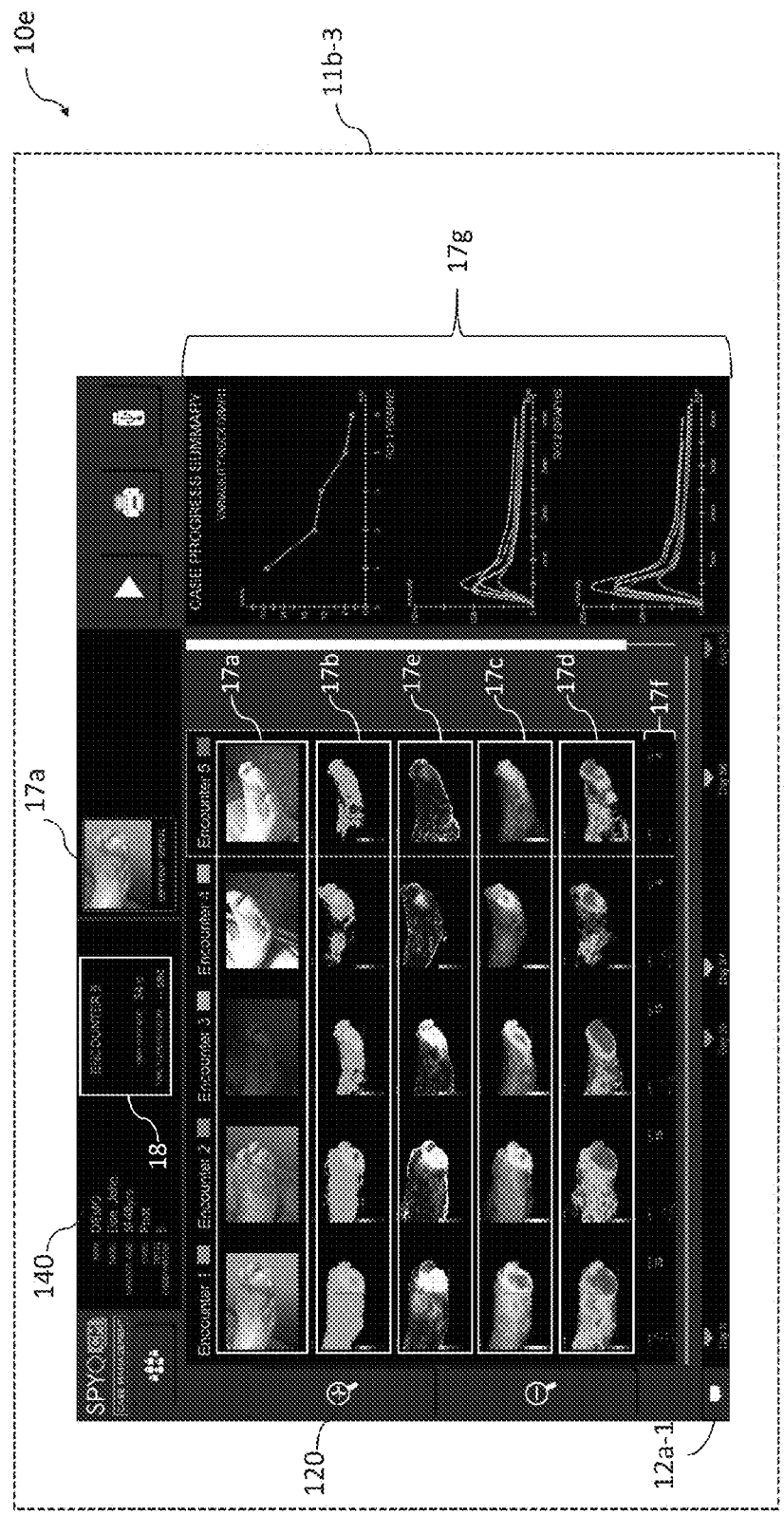
FIG. 3C illustrates example clinical image data generated by a fluorescence imaging system, and management of such data derived from fluorescence imaging according to an embodiment.

In some embodiments, a user may select an encounter of interest in order to view additional information generated during the encounter. For example, user interface 11b-3 of FIG. 3C illustrates selection of Encounter 5, as shown by the vertical rectangle encompassing the data view elements associated with Encounter 5. In response to this selection, auxiliary data element 18 is displayed. This element may include any information generated during the associated encounter, such as blood pressure. In the embodiment of FIG. 3C, skin surface temperature and time to perfusion are included in the auxiliary data element 18 for illustration. In some embodiments, the curves of data view element 17g that are associated with the selected encounter may be emphasized, for example, by increasing the respective line thickness.

In some embodiments of a case management user interface such as user interface 11b of FIG. 2, a timeline associated with the series of encounters for which image data is shown may be included. Exemplary timelines are shown in each of FIGS. 3A-3C beneath the data view elements. According to one embodiment, a control element may be included in one of control element regions 12a-c to allow insertion of textual timeline notes corresponding to specific dates and which may be indicated by an icon shown on the timeline. This is shown, for example, as note icon 12a-1 in FIGS. 3B and 3C. For example, additional relevant information such as details of a subject's fall occurring between encounter dates could be added as a timeline note. Information in timeline notes may help the user to interpret changes seen in subject data between encounters, or case progress summary data over time.

According to an embodiment of a case management user interface, additional descriptive text or icons may be displayed between or within encounter columns, for example to indicate treatment information. In one example, treatment information may be conveyed with vertical text displayed alongside each encounter column.

Figure 4A:
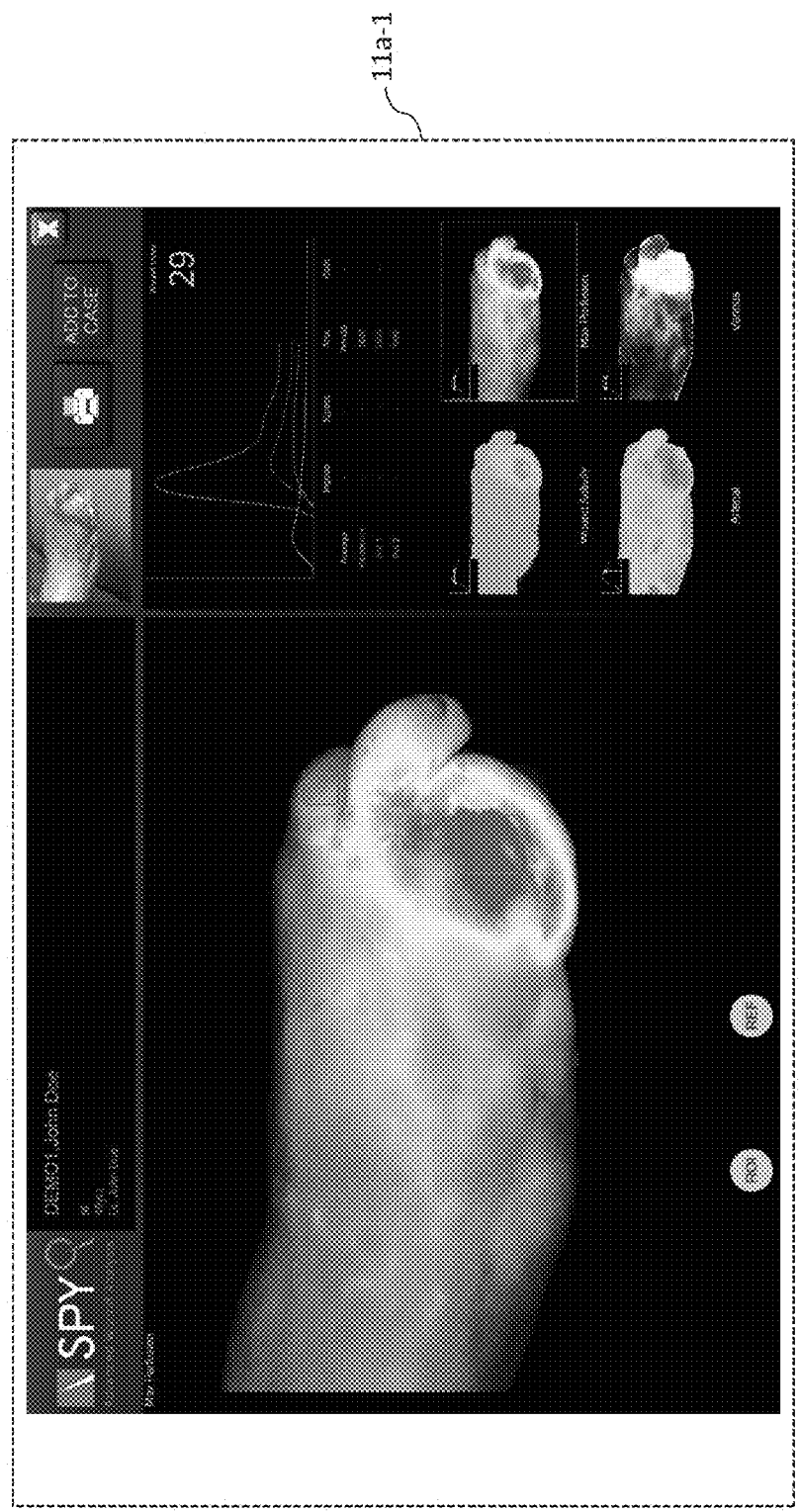
FIG. 4A illustrates example clinical image data generated by a fluorescence imaging system, and management of such data derived from fluorescence imaging according to an embodiment.

In some embodiments, a user may select a data view element, for example, in any of user interfaces 11b-1 through 11b-3, to focus on the selected data view element and on the encounter of the selected data view element. For example, a user may select the maximum perfusion data view element 17c for Encounter 1, and in response, user interface 11a-1 of FIG. 4A may be displayed. FIG. 4A illustrates that the user can zoom in on a particular data view element 16 to extract further data (e.g., in the region of interest and/or a reference region indicated with squares in the image) while at the same time being able to view the corresponding maps or images of other data view elements 16, and other numerical and/or graphical data view elements 16 such as the wound index value (e.g., value 29 in FIG. 4A) and time-intensity curves. The selected data view element (maximum perfusion in FIG. 4A) is shown enlarged while other data views are shown smaller. In some embodiments, a user may select one of the other data view elements that are shown smaller in order to switch to an enlarged view of the selected data view. Thus, a user may sequentially transition to focused views of each of the data view elements for a given encounter without returning to the user interface of FIGS. 3A-3C.

In this example, each graph display contains a wound index number for the regions of interest, which if created by the user, may be combined and displayed from each visit. Thus, for example, ingress, egress, region of interest area and comparison of data with each visit may be compared to the previous on a single display.

In some embodiments, user interface 11a-1 may be used to select one or more regions of interest within a data view element. Two regions of interest are shown in FIG. 4A ("ROI 1" and "ROI 2"). Regions of interest may be defined in numerous ways. For example, a user may tap or click a portion of the zoomed-in view element to place a region of interest box. The user may then resize the box, for example, using drag operation. Regions of interest may also be defined automatically or semi-automatically (eg., with parameters set by user input), based on analysis of attribute data from one or more of the data views, for example according to attribute values exceeding a threshold value. According to some embodiments, a user may select a region of interest icon (such as the "ROI" icon shown at the bottom of the user interface in FIG. 4A) to initiate setting of one or more regions of interest. In some embodiments, a "reference" region may be defined to provide a baseline for comparison with the regions of interest. For example, FIG. 4A includes a reference region located at a distance from the regions of interest. The selection of the reference region may be performed similarly to the selection of regions of interest. For example, a user may select the "REF" icon in FIG. 4A to initiate the setting of the reference region. Once the region(s) of interest and reference region (if used) are set, they may be automatically duplicated across all data view elements for the associated encounter. One or more graphs may be generated to illustrate one or more characteristics of the defined region(s) of interest. For example, the graph in FIG. 4A illustrates the average intensity (within each region area) of the maximum perfusion of the regions of interest as a function of the encounter time.

In some embodiments, one or more scroll bars may be used in user interface 11a-1 to navigate around the zoomed-in view. In other embodiments, a user may pan around the zoomed-in view, for example, with a drag gesture or any other method of navigating to partially hidden portions of a view.

According to some embodiments of an analysis user interface, such as user interface 11a of FIG. 1, a control element may comprise a button or other user interface object that a user may interact with to display one or more contour lines on the selected (enlarged) image map. These contour lines may then remain visible when displaying other image maps or the white light image, thus facilitating inspection of a particular area of interest, as indicated by one image map, according to multiple image data perspectives.

Figure 4B:
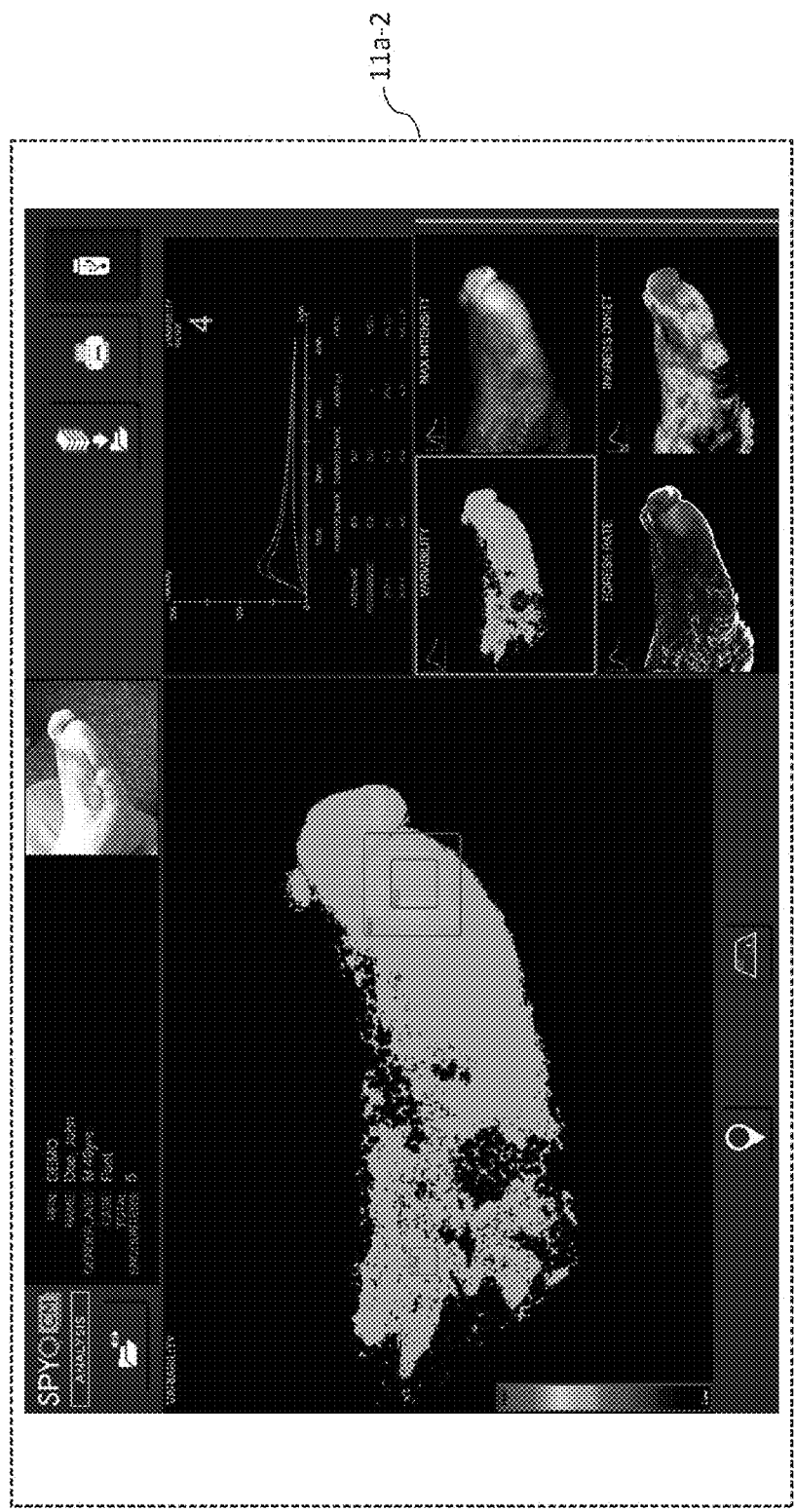
FIG. 4B illustrates example clinical image data generated by a fluorescence imaging system, and management of such data derived from fluorescence imaging according to an embodiment.

FIG. 4B illustrates another embodiment of a zoomed-in data element user interface. In user interface 11a-2 of this embodiment, the variability data view (also referred to as "wound activity") is shown enlarged along with a color scale (in which a variability data view is provided). In this view, two overlapping regions of interest are shown.

In some embodiments, a control element may be included in a zoomed-in user interface, such as user interfaces 11a-1 or 11a-2 to directly navigate through zoomed-in views of multiple encounters. For example, left and right arrows may be used to move from one encounter to the immediate next or previous encounter without returning to the user interface of FIGS. 3A-3C.

Figure 5A:
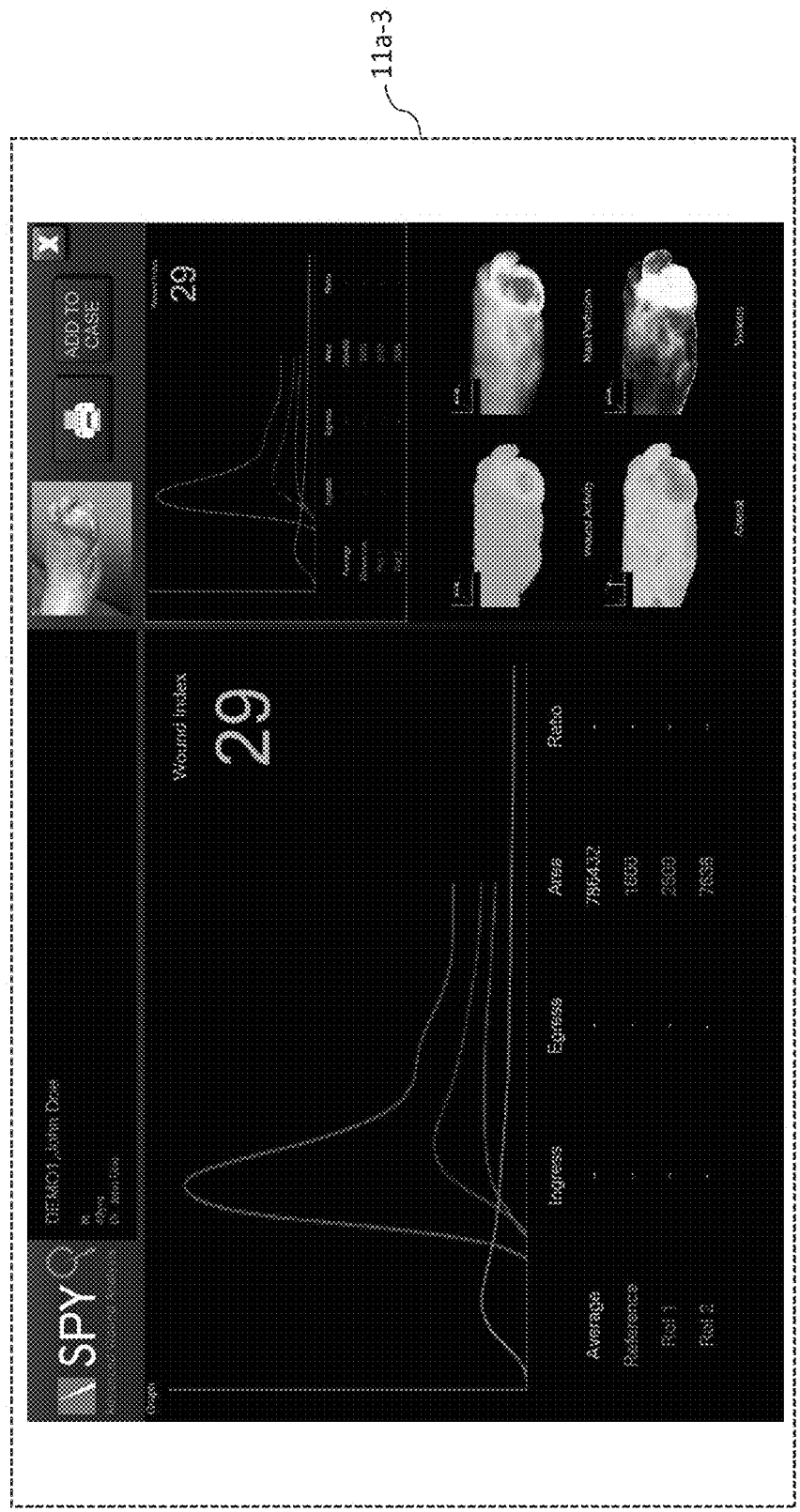
FIG. 5A illustrates example clinical image data generated by a fluorescence imaging system, and management of such data derived from fluorescence imaging according to an embodiment.
Figure 5B:
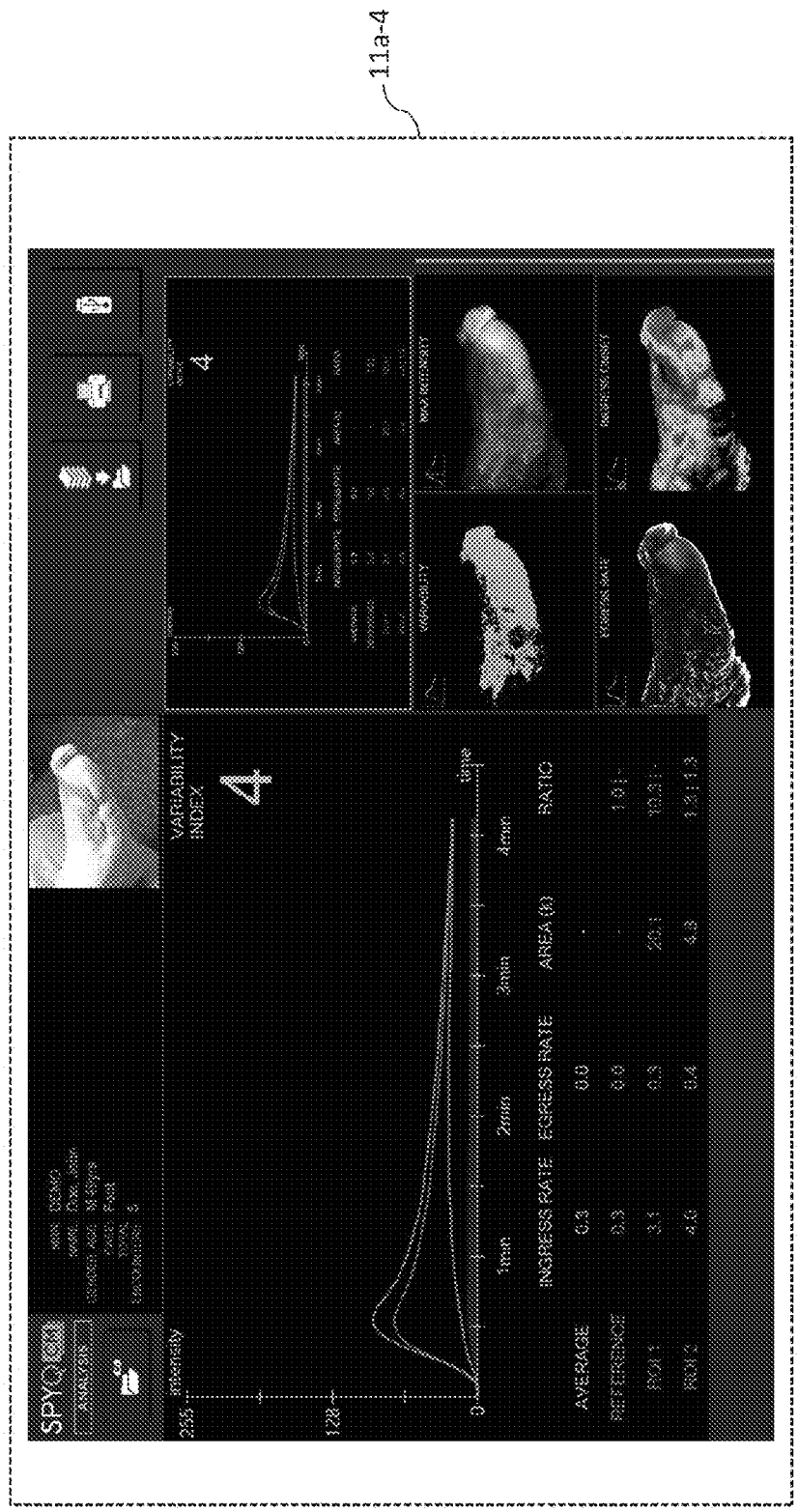
FIG. 5B illustrates example clinical image data generated by a fluorescence imaging system, and management of such data derived from fluorescence imaging according to an embodiment.

FIG. 5A illustrates yet another user interface 11a-3 of the data in FIG. 3A. In FIG. 5A, an intensity graph is selected for zoomed-in viewing and is displayed enlarged. The intensity graph provides intensities across the regions of interest and reference region for each of the wound activity, max perfusion, arterial and venous characteristics. FIG. 5B illustrates an alternative user interface 11a-4 in which the intensity graph is zoomed-in. In this embodiment, "Wound Activity" is relabeled "Variability," "Max Perfusion" is relabeled as "Max Intensity," "Arterial" is relabeled as "Ingress Onset," and "Venous" is relabeled as "Egress Rate."

Beneath the enlarged graph in user interface 11a-4 of FIG. 5B, a data summary is provided. Here the "AREA" represents the area of a specific clinical feature, for example the area of a wound, and may be estimated by data from one of the image maps, by using the area of a manually defined region of interest, or by any other algorithm applied to the imaging data. The "RATIO" displayed corresponds to the ratio of ROI 1 values to REFERENCE values (shown in ROI 1 row) and the ratio of ROI 2 values to ROI 1 values (shown in ROI 2 row). The two ratio values shown in each row correspond to ingress rate ratio (left) and egress rate ratio (right), which are shown separated by "|".

It would be understood that in various embodiments the data view elements 16 as concurrently displayed can comprise any one or more of the data view elements in a selected combination. For example, with reference to FIG. 3A, some or all of the five data view elements 160a, 160b, 160c, 160d, and 160e may be concurrently displayed in a selected combination such as, for example, [160a+160b+160c+160d+160e], [160a+160b+160c], or [160b+160c+160e]. The choice of the particular selected combination may be dictated by the clinical circumstances to provide custom tailored assessment for that particular clinical circumstance and to optimize extraction of the most clinically relevant insights for the case at issue. For example, a clinical case relating to an occlusive vascular disease wound may present an entirely different combination of the data view elements 16 than a clinical case relating to a subject with diabetes. Thus, depending on the clinical circumstances, certain data viewing elements 16 in the concurrent display may be emphasized or of less importance, which is user selectable.

The user interfaces described herein are intended to be agnostic to the types of subject data and image maps displayed in the user interface screens, and are merely shown with sample data and image maps corresponding to an example wound care application, but could also include data from other clinical applications such as, for example, a cardiac imaging or intervention application, or other data or image maps from a wound care application.

According to another aspect of the invention there is provided a method for management of data derived from medical imaging. The method comprises providing a user interface on a display screen, the user interface configured to display a control element operable by a user, a subject identifier element for identifying the subject, and a data view element for viewing the data, wherein the data view element is displayed simultaneously for an initial assessment and one or more subsequent assessments of a tissue of a subject, or for two or more subsequent assessments following the initial assessment to facilitate observing a change in the tissue over time. Various aspects of the method are similar to the corresponding aspects described above in connection with the system for management of data derived from medical imaging.

Figure 9:
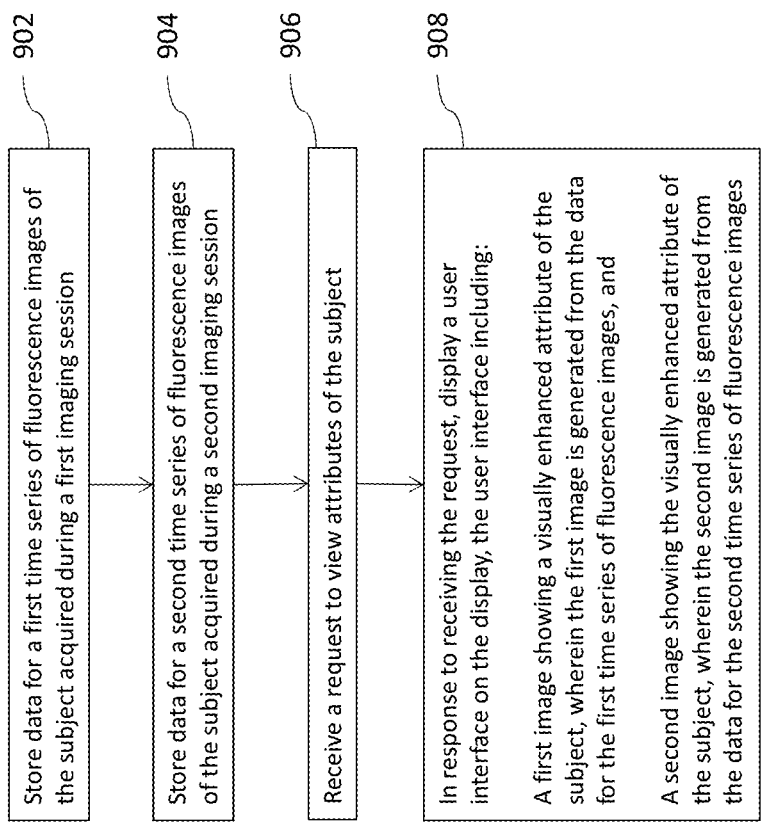
FIG. 9 is an illustrative block diagram of an exemplary method for management of data derived from medical imaging according to an embodiment.

FIG. 9 illustrates method 900 for displaying data derived from medical imaging, according to some embodiments. Method 900 may be performed by a computing system having one or more processors, memory, and a display. The computing system may include one or more input devices such as a touch screen, keyboard, mouse, etc. At step 902, data for a first time series of fluorescence images of a subject acquired during a first imaging session is stored. The data may be based on data generated by a fluorescence imaging system such as fluorescence imaging system 20 of FIG. 6 during the first imaging session. For example, the data may include a time series of signal intensity data capturing the transit of a fluorescence imaging agent through tissue of the subject within a field of view of the imaging system over a period of time (e.g., over several second or over several minutes, or any other time period).

At step 904, data for a second time series of fluorescence images of the subject acquired during a second imaging session may be stored. Similarly to the data stored in step 902, the data stored at step 904 may be based on data generated by a fluorescence imaging system such as fluorescence imaging system 20 of FIG. 6 during the second imaging session.

The data stored at steps 902 and 904 may be raw image data or may be pre-processed data generated by pre-processing raw image data.

At step 906, a request to view attributes of the imaged subject is received. The request may be received through one or more user interfaces on the display. For example, a user interface may display a list of subjects, and a user may select the subject of interest from the list. The selection may be made via, for example, a tap on a touch screen, a click of a mouse, or any other conventional method. In some embodiments, the request to view attributes of the imaged subject is received prior to steps 902 and 904. In response to the request, the data associated with the subject may be retrieved, for example, from an external system and loaded into memory. In some embodiments, some of the data associated with the subject may be stored locally while some other data associated with the subject may be retrieved from an external system. For example, data associated with one or more sessions may be stored on the system and, in response to the request, the system may check whether additional data has been generated for the subject, such as during a more recent imaging session. If there is additional data, the system may retrieve the additional data and associate the additional data with the previously stored data.

At step 908, in response to receiving the request to view attributes of the imaged subject, a user interface is displayed on the display. The user interface includes a first image showing a visually enhanced attribute of the subject, wherein the first image is generated from the data for the first time series of fluorescence images. The user interface also includes a second image showing the visually enhanced attribute of the subject, wherein the second image is generated from the data for the second time series of fluorescence images. Examples of a user interface that may be displayed at step 908 include user interfaces 11*b*-1 through 11*b*-3 of FIGS. 3A through 3C. With respect to FIG. 3A, a first image may be the maximum intensity image shown in data view element 160*c* for assessment "Visit 1" and the second image may be the maximum intensity image shown in data view element 160*c* for assessment "Visit 2." In this case, the attribute is the maximum intensity reached during the entire measurement period. As illustrated in FIG. 3A, the maximum intensity images are visually enhanced by using color contrast to represent the range of intensity values. In some embodiments, grayscale contrast may be used. The first image represents the attribute of the subject at the time of the first imaging session and the second image represents the attribute of the subject at the time of the second imaging session. By visually comparing the two images, a clinician can easily assess, for example, the healing progress of the imaged tissue.

According to some embodiments, a plurality of images associated with an imaging session may be displayed, with each image representing a different attribute. For example, each of the data view elements 16*b*-16*e* include images of different types of attributes. The plurality of images may be displayed for each of a plurality of assessment visits. Images of the same type may be aligned (for example, vertically or horizontally aligned) to facilitate easy comparison.

In some embodiments, the images may be scrolled to reveal additional images, such as additional image types or images from additional assessment visits, for example, when all images cannot fit within user interface. Images may be scrolled using a touch gesture such as a drag or swipe on the portion of the user interface that includes the images or may be scrolled using one or more scroll bars.

In some embodiments, the user interface may include additional information generated from the data stored at steps 902 and 904 such as one or more graphs or textual information generated based on the stored data. In some embodiments, a graph may include curves associated with each of the assessment visits to enable easy graphical comparison of the state of the imaged tissue or imaged anatomical portion of the subject. For example, a graph of variability index values may be displayed that shows the change in variability index of the anatomical view or portion of the anatomical across the assessment visits.

In some embodiments, method 900 may include receiving a selection of the first image and, in response, enlarging the first image. In some embodiments, the enlarged first image may be displayed by replacing display of the user interface that comprises the first and second images with a user interface for displaying details of the encounter of the selected first image. For example, the user interface of FIG. 2 may be replaced by the user interface of FIG. 1 with the enlarged first image displayed in the "dashboard work surface" area of the user interface, as shown in FIGS. 4A and 4B.

In some embodiments, the enlarged first image may be used to define a region of interest, which may be initiated via selection of one or more user interface objects, such as the "ROI" icon in FIG. 4A. In some embodiments, a reference region may be defined, for example, via selection of the "REF" icon in FIG. 4A. In some embodiments, method 900 may include generating one or more graphs of metrics of the attribute of the subject within the region of interest for the first image.

In some embodiments, the user interface with the enlarged first image may include other images associated with the first imaging session (for example, providing additional visually enhanced attributes) and method 900 may include receiving a selection of one of the other images and replacing the enlarged first image with an enlarged selected image. For example, with reference to FIG. 4A, the enlarged max perfusion image may be replaced by an enlarged wound activity image in response to a user selection of the smaller wound activity image in the lower right portion of user interface 11*a*-1.

Figure 10:
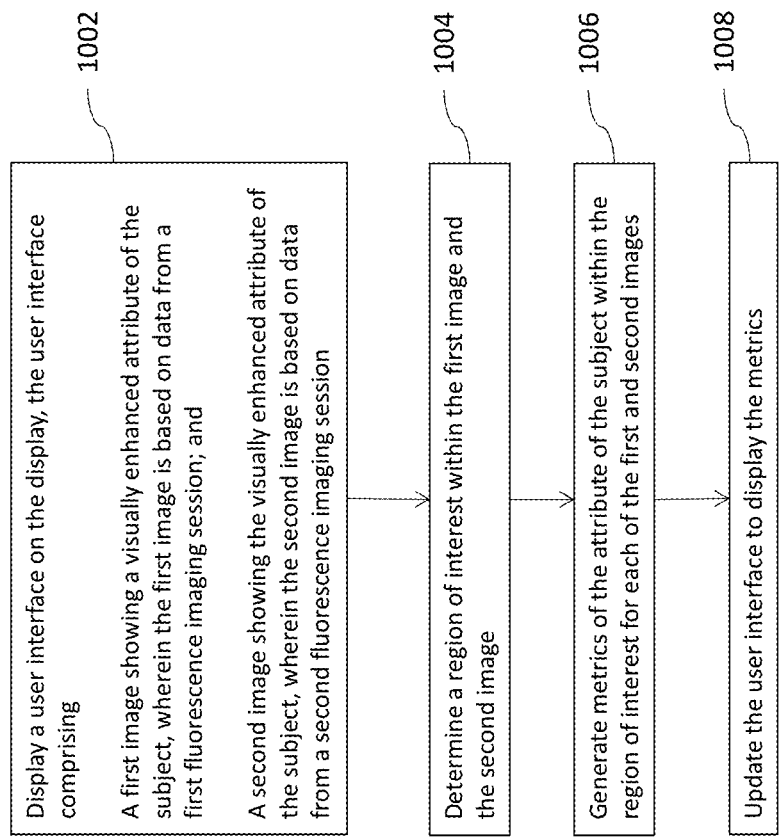
FIG. 10 is an illustrative block diagram of an exemplary method for management of data derived from medical imaging according to an embodiment.

FIG. 10 illustrates method 1000 for displaying data derived from medical imaging, according to some embodiments. Method 1000 may be performed by a computing system having one or more processors, memory, and a display. The computing system may include one or more input devices such as a touch screen, keyboard, mouse, etc. At step 1002, a user interface is displayed on the display, the user interface includes a first image showing a visually enhanced attribute of the subject, wherein the first image is based on data from a first fluorescence imaging session; and a second image showing the visually enhanced attribute of the subject, wherein the second image is based on data from a second fluorescence imaging session. The first and second images may be substantially similar to those discussed above with respect to step 908 of method 900.

At step 1004, a region of interest within the first image and the second image is determined. The region of interest is a spatial region encompassing at least a portion of the image. In this step, a region of interest is determined for each of the first and second images. The locations and sizes of regions of interest may be identical from the first image to the second image or may vary from the first image to the second image. In some embodiments, the region of interest is predefined and in other embodiments, the region of interest is defined by a user. For example, a user may insert a bounding box into the first and/or second images at a location and with a size to define the region of interest. In some embodiments, the user defines a first region of interest for the first image and a second region of interest for the second image. In some embodiments, the user can move or resize the region of interest, for example, via one or more panning gestures, dragging gestures, pinching gestures, or any other conventional user inputs to position and resize a graphical object in a user interface.

In some embodiments, the user interface includes a third image that is generated based on the data from the first imaging session and provides a different attribute than the first image. Upon defining the region of interest within the first image, a region of interest may be automatically defined for the third image.

At step 1006, metrics of the attribute of the subject within the region of interest are generated for each of the first and second images. For example, a variability index value for the region of interest in the first image and a variability index value for the region of interest in the second image may be generated.

At step 1008, the user interface is updated to display the generated metrics. An example of displayed metrics is the variability index graph provided in user interface 11*b*-2 of FIG. 3B. In the graph, variability index metrics have been computed for the regions of interest of each of the five encounters and have been plotted on the graph.

FIG. 11 illustrates an example of a computing device in accordance with some embodiments (for example, any of systems 10*a*-10*e*, 20, 30, or 50), or a computing device for implementing methods 900 and 1000). Device 1100 can be a host computer connected to a network. Device 1100 can be a client computer or a server. As shown in FIG. 11, device 1100 can be any suitable type of microprocessor-based device, such as a personal computer, workstation, server, or handheld computing device (portable electronic device) such as a phone or tablet. The device can include, for example, one or more of processor 1110, input device 1120, output device 1130, storage 1140, and communication device 1160. Input device 1120 and output device 1130 can generally correspond to those described above and can either be connectable or integrated with the computer.

Input device 1120 can be any suitable device that provides input, such as a touch screen, keyboard or keypad, mouse, or voice-recognition device. Output device 1130 can be any suitable device that provides output, such as a touch screen, haptics device, or speaker.

Storage 1140 can be any suitable device that provides storage, such as an electrical, magnetic, or optical memory including a RAM, cache, hard drive, or removable storage disk. Communication device 1160 can include any suitable device capable of transmitting and receiving signals over a network, such as a network interface chip or device. The components of the computer can be connected in any suitable manner, such as via a physical bus or wirelessly.

Software 1150, which can be stored in storage 1140 and executed by processor 1110, can include, for example, the programming that embodies the functionality of the present disclosure (e.g., as embodied in the devices as described above).

Software 1150 can also be stored and/or transported within any non-transitory computer-readable storage medium for use by or in connection with an instruction execution system, apparatus, or device, such as those described above, that can fetch instructions associated with the software from the instruction execution system, apparatus, or device and execute the instructions. In the context of this disclosure, a computer-readable storage medium can be any medium, such as storage 1140, that can contain or store programming for use by or in connection with an instruction execution system, apparatus, or device.

Software 1150 can also be propagated within any transport medium for use by or in connection with an instruction execution system, apparatus, or device, such as those described above, that can fetch instructions associated with the software from the instruction execution system, apparatus, or device and execute the instructions. In the context of this disclosure, a transport medium can be any medium that can communicate, propagate or transport programming for use by or in connection with an instruction execution system, apparatus, or device. The transport readable medium can include, but is not limited to, an electronic, magnetic, optical, electromagnetic, or infrared wired or wireless propagation medium.

Device 1100 may be connected to a network, which can be any suitable type of interconnected communication system. The network can implement any suitable communications protocol and can be secured by any suitable security protocol. The network can comprise network links of any suitable arrangement that can implement the transmission and reception of network signals, such as wireless network connections, T1 or T3 lines, cable networks, DSL, or telephone lines.

Device 1100 can implement any operating system suitable for operating on the network. Software 1150 can be written in any suitable programming language, such as C, C++, Java, or Python. In various embodiments, application software embodying the functionality of the present disclosure can be deployed in different configurations, such as in a client/server arrangement or through a Web browser as a Web-based application or Web service, for example.

Thus, the systems and methods in accordance with the various embodiments provide an intuitive and user friendly user interface with modality-specific workflows which facilitate access to advanced analysis tools for inexperienced and experienced users, which may be used in the analysis of blood flow dynamics, including tissue perfusion analysis. Tissue perfusion relates to the microcirculatory flow of blood per unit tissue volume in which oxygen and nutrients are provided to and waste is removed from the capillary bed of the tissue being perfused. A distinction should be drawn between vascular blood flow and tissue blood perfusion, namely that tissue perfusion is a phenomenon related to but also distinct from blood flow in vessels. Quantified blood flow through blood vessels is expressed in terms that define flow (i.e., volume/time), or that define speed (i.e., distance/time). Tissue blood perfusion defines movement of blood through blood vessels within a tissue volume. Quantified tissue blood perfusion is expressed in terms of blood, namely, that of volume/time/tissue volume. Perfusion is associated with nutritive blood vessels (i.e., micro-vessels known as capillaries) that comprise the vessels associated with exchange of metabolites between blood and tissue, rather than larger-diameter non-nutritive vessels. However, compared to blood movement through the larger diameter blood vessels, blood movement through individual capillaries can be highly erratic, principally due to vasomotion, wherein spontaneous oscillation in blood vessel tone manifests as pulsation in erythrocyte movement.

While the present disclosure has been illustrated and described in connection with various embodiments shown and described in detail, it is not intended to be limited to the details shown, since various modifications and structural changes may be made without departing in any way from the scope of the present disclosure. Various modifications of form, arrangement of components, steps, details and order of operations of the embodiments illustrated, as well as other embodiments of the disclosure may be made without departing in any way from the scope of the present disclosure, and will be apparent to a person of skill in the art upon reference to this description. It is therefore contemplated that the appended claims will cover such modifications and embodiments as they fall within the true scope of the disclosure. For the purpose of clarity and a concise description, features are described herein as part of the same or separate embodiments; however, it will be appreciated that the scope of the disclosure includes embodiments having combinations of all or some of the features described. For the terms "for example" and "such as," and grammatical equivalences thereof, the phrase "and without limitation" is understood to follow unless explicitly stated otherwise. As used herein, the singular forms "a", "an", and "the" include plural referents unless the context clearly dictates otherwise.

What is claimed is:

1. A system comprising:
a display for displaying an attribute of tissue of a subject;
one or more processors;
memory;
one or more programs stored in the memory and configured to be executed by the one or more processors, the one or more programs including instructions for:
storing data for a first time series of fluorescence images of the tissue of the subject acquired during a first imaging session;
storing data for a second time series of fluorescence images of the tissue of the subject acquired during a second imaging session;
receiving a request to view attributes of the subject; and
in response to receiving the request, displaying a user interface on the display, the user interface comprising:
a first image of the tissue of the subject showing a visually enhanced attribute of the tissue of the subject, wherein the first image is generated from the data for the first time series of fluorescence images such that the first image illustrates a state of the tissue at the time of the first imaging session, and
a second image of the tissue of the subject showing the visually enhanced attribute of the tissue of the subject, wherein the second image is generated from the data for the second time series of fluorescence images such that the second image illustrates the state of the tissue at the time of the second imaging session.

2. The system of claim 1, wherein the first and second images comprise a maximum perfusion image or map, a maximum fluorescence intensity image or map, a coefficient-derived image or map, a fluorescence intensity variability image or map, an egress rate image or map, an ingress onset image or map, or a combination thereof.

3. The system of claim 1, wherein the first and second images comprise color contrast.

4. The system of claim 1, wherein the first and second images comprise grayscale contrast.

5. The system of claim 1, including instructions for receiving a selection of the first image and, in response to receiving the selection, enlarging the first image.

6. The system of claim 5, including instructions for receiving a selection of the second image and replacing the enlarged first image with an enlarged second image.

7. The system of claim 1, wherein at least some of the data for the first time series and at least some of the data for the second time series comprises raw data, pre-processed data or a combination thereof.

8. The system of claim 7, wherein the pre-processed data is generated by one or more of cropping, spatially aligning, and determination of baseline intensity.

9. The system of claim 1, wherein the user interface comprises a graph of a characteristic of a region of interest within at least one of the first image and the second image.

10. The system of claim 9, wherein the graph comprises a change in intensity over time that is indicative of a healing state of tissue of the subject.

11. The system of claim 9, wherein the graph comprises a first curve associated with the first image and a second curve associated with the second image.

12. The system of claim 1, wherein the user interface includes a quantification of a healing state of tissue of the subject associated with each imaging session.

13. The system of claim 1, wherein a pixel value of the first image is calculated from corresponding pixel values of the first time series of fluorescence images.

14. The system of claim 1, including instructions for, in response to receiving the request, calculating a baseline from the data for the first time series of fluorescence images and the data for the second time series of fluorescence images, wherein the first and second images are generated based on the baseline.

15. The system of claim 14, wherein the baseline is calculated from a minimum intensity value or an average intensity value for both of the data for the first time series of fluorescence images and the data for the second time series of fluorescence images.

16. The system of claim 1, wherein the first image is scaled to a range of values and the second image is scaled to the range of values.

17. The system of claim 1, wherein the system is a handheld electronic device.

18. A method comprising, at a computer system comprising one or more processors, memory, and a display:
storing data for a first time series of fluorescence images of tissue of a subject acquired during a first imaging session;
storing data for a second time series of fluorescence images of the tissue of the subject acquired during a second imaging session;
receiving a request to view attributes of the subject; and
in response to receiving the request, displaying a user interface on the display, the user interface comprising:
a first image of the tissue of the subject showing a visually enhanced attribute of the tissue of the subject, wherein the first image is generated from the data for the first time series of fluorescence images such that the first image illustrates a state of the tissue at the time of the first imaging session, and a second image of the tissue of the subject showing the visually enhanced attribute of the tissue of the subject, wherein the second image is generated from the data for the second time series of fluorescence images such that the second image illustrates the state of the tissue at the time of the second imaging session.

19. A non-transitory computer readable storage medium storing one or more programs, the one or more programs comprising instructions, which when executed by an electronic system with a display, cause the system to perform a method comprising:

storing data for a first time series of fluorescence images of tissue of a subject acquired during a first imaging session;

storing data for a second time series of fluorescence images of the tissue of the subject acquired during a second imaging session;

receiving a request to view attributes of the subject; and in response to receiving the request, displaying a user interface on the display, the user interface comprising:

a first image of the tissue of the subject showing a visually enhanced attribute of the tissue of the subject, wherein the first image is generated from the data for the first time series of fluorescence images such that the first image illustrates a state of the tissue at the time of the first imaging session, and a second image of the tissue of the subject showing the visually enhanced attribute of the tissue of the subject, wherein the second image is generated from the data for the second time series of fluorescence images such that the second image illustrates the state of the tissue at the time of the second imaging session.

20. A system comprising:

a display;

one or more processors;

memory;

one or more programs stored in the memory and configured to be executed by the one or more processors, the one or more programs including instructions for:

displaying a user interface on the display, the user interface comprising:

a first image of tissue of a subject showing a visually enhanced attribute of the tissue of the subject, wherein the first image is based on data from a first fluorescence imaging session such that the first image illustrates a state of the tissue at the time of the first imaging session, and a second image of the tissue of the subject showing the visually enhanced attribute of the subject, wherein the second image is based on data from a second fluorescence imaging session such that the second image illustrates the state of the tissue at the time of the second imaging session;

determining a region of interest within the first image and the second image;

generating metrics of the attribute of the tissue of the subject within the region of interest for each of the first and second images; and updating the user interface to display the metrics.

21. The system of claim 20, wherein the region of interest within the first image is determined based on an input by the user.

22. The system of claim 21, wherein the input by the user comprises insertion of a first bounding box on a portion of the user interface associated with the region of interest for the first image.

23. The system of claim 22, wherein the user interface comprises a third image that is based on data from the first fluorescence imaging session, and the one or more programs include instructions for automatically inserting a second bounding box on a portion of the user interface associated with the region of interest of the second image.

24. The system of claim 20, wherein the first and second images comprise a maximum perfusion image or map, a maximum fluorescence intensity image or map, a coefficient-derived image or map, a fluorescence intensity variability image or map, an egress rate image or map, an ingress onset image or map, or a combination thereof.

25. The system of claim 20, wherein the first and second images comprise color contrast.

26. The system of claim 20, wherein the first and second images comprise grayscale contrast.

27. A method comprising, at a computer system comprising one or more processors, memory, and a display:

displaying a user interface on the display, the user interface comprising:

a first image of tissue of a subject showing a visually enhanced attribute of the tissue of the subject, wherein the first image is based on data from a first fluorescence imaging session such that the first image illustrates a state of the tissue at the time of the first imaging session, and a second image of the tissue of the subject showing the visually enhanced attribute of the subject, wherein the second image is based on data from a second fluorescence imaging session such that the second image illustrates the state of the tissue at the time of the second imaging session;

determining a region of interest within the first image and the second image;

generating metrics of the attribute of the tissue of the subject within the region of interest for each of the first and second images; and updating the user interface to display the metrics.

28. A non-transitory computer readable storage medium storing one or more programs, the one or more programs comprising instructions, which when executed by an electronic system with a display, cause the system to perform a method comprising:

displaying a user interface on the display, the user interface comprising:

a first image of tissue of a subject showing a visually enhanced attribute of the tissue of the subject, wherein the first image is based on data from a first fluorescence imaging session such that the first image illustrates a state of the tissue at the time of the first imaging session, and a second image of the tissue of the subject showing the visually enhanced attribute of the subject, wherein the second image is based on data from a second fluorescence imaging session such that the second image illustrates the state of the tissue at the time of the second imaging session;

determining a region of interest within the first image and the second image;

generating metrics of the attribute of the tissue of the subject within the region of interest for each of the first and second images; and updating the user interface to display the metrics.

29. A system comprising:
a display;
one or more processors;
memory;
one or more programs stored in the memory and configured to be executed by the one or more processors, the one or more programs including instructions for:
displaying a user interface on the display, the user interface comprising a first image of tissue of the subject showing a first visually enhanced attribute of the tissue of the subject and a second image of the tissue of the subject showing a second visually enhanced attribute of the tissue of the subject, wherein the first and second images are based on data from a fluorescence imaging session;
determining a region of interest within the first image;
generating metrics of the first attribute of the subject within the region of interest; and
updating the user interface to display the metrics.

30. The system of claim 29, wherein the region of interest within the first image is determined based on an input by a user.

31. The system of claim 30, wherein the input by the user comprises insertion of a first bounding box on a portion of the user interface associated with the region of interest within the first image.

32. The system of claim 29, wherein the one or more programs include instructions for:
receiving a user input for selecting the second image; and
in response to receiving the user input, replacing display of the first image with an enlarged second image.

33. The system of claim 32, wherein the one or more programs include instructions for automatically determining a region of interest within the second image based on the region of interest within the first image.

34. The system of claim 29, wherein the first image comprises a maximum perfusion image or map, a maximum fluorescence intensity image or map, a coefficient-derived image or map, a fluorescence intensity variability image or map, an egress rate image or map, an ingress onset image or map, or a combination thereof.

35. The system of claim 29, wherein the first image comprises color contrast.

36. The system of claim 29, wherein the first image comprises grayscale contrast.

37. A method comprising, at a computer system comprising one or more processors, memory, and a display:
displaying a user interface on the display, the user interface comprising a first image of tissue of a subject showing a first visually enhanced attribute of the tissue of the subject and a second image of the tissue of the subject showing a second visually enhanced attribute of the tissue of the subject, wherein the first and second images are based on data from a fluorescence imaging session;
determining a region of interest within the first image;
generating metrics of the first attribute of the subject within the region of interest; and
updating the user interface to display the metrics.

38. A non-transitory computer readable storage medium storing one or more programs, the one or more programs comprising instructions, which when executed by an electronic system with a display, cause the system to perform a method comprising:
displaying a user interface on the display, the user interface comprising a first image of tissue of a subject showing a first visually enhanced attribute of the tissue of the subject and a second image of the tissue of the subject showing a second visually enhanced attribute of the tissue of the subject, wherein the first and second images are based on data from a fluorescence imaging session;
determining a region of interest within the first image;
generating metrics of the first attribute of the subject within the region of interest; and
updating the user interface to display the metrics.

39. The system of claim 1, wherein the user interface displays the visually enhanced attribute of the tissue of the subject in combination with an attribute of the subject.

40. The system of claim 20, wherein the user interface displays the visually enhanced attribute of the tissue of the subject in combination with an attribute of the subject.

41. The system of claim 29, wherein the user interface displays the visually enhanced attribute of the tissue of the subject in combination with an attribute of the subject.

* * * * *